United States Patent
Choi et al.

(10) Patent No.: US 9,546,952 B2
(45) Date of Patent: Jan. 17, 2017

(54) DISTRIBUTION OF REFRACTIVE INDEX MEASUREMENT BY SYNTHETIC APERTURE TOMOGRAPHY

(71) Applicant: Massachusetts Institute of Technology, Cambridge, MA (US)

(72) Inventors: Wonshik Choi, Somerville, MA (US); Ramachandra Dasari, Shererville, IN (US); Christopher Fang-Yen, Philadelphia, PA (US); Michael Feld, Jamaica Plain, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 91 days.

(21) Appl. No.: 14/490,242

(22) Filed: Sep. 18, 2014

(65) Prior Publication Data
US 2015/0177133 A1 Jun. 25, 2015

Related U.S. Application Data

(62) Division of application No. 12/218,029, filed on Jul. 10, 2008, now Pat. No. 8,848,199.
(Continued)

(51) Int. Cl.
| | |
|---|---|
| *G01N 21/45* | (2006.01) |
| *G01N 21/51* | (2006.01) |
| *G01N 21/64* | (2006.01) |

(52) U.S. Cl.
CPC ............ *G01N 21/45* (2013.01); *G01N 21/51* (2013.01); *G01N 21/6458* (2013.01);
(Continued)

(58) Field of Classification Search
CPC .... G01N 21/45; G01N 21/6486; G01N 21/51; G01N 21/6458
See application file for complete search history.

(56) References Cited

U.S. PATENT DOCUMENTS

| 5,633,714 A | 5/1997 | Nyyssonen |
|---|---|---|
| 7,365,858 B2 | 4/2008 | Fang-Yen et al. |

(Continued)

FOREIGN PATENT DOCUMENTS

| WO | WO-2005/001445 | 1/2005 |
|---|---|---|
| WO | 2006010253 A1 | 2/2006 |
| WO | WO-2007/116365 | 12/2007 |

OTHER PUBLICATIONS

International Preliminary Report on Patentability by the International Bureau of WIPO for International Application PCT/US2008/008447 dated Jan. 12, 2010. (24 pages).
(Continued)

*Primary Examiner* — Hwa Lee
(74) *Attorney, Agent, or Firm* — McCarter & English, LLP

(57) ABSTRACT

The present invention relates to systems and methods for quantitative three-dimensional mapping of refractive index in living or non-living cells, tissues, or organisms using a phase-shifting laser interferometric microscope with variable illumination angle. A preferred embodiment provides tomographic imaging of cells and multicellular organisms, and time-dependent changes in cell structure and the quantitative characterization of specimen-induced aberrations in high-resolution microscopy with multiple applications in tissue light scattering.

30 Claims, 23 Drawing Sheets

Related U.S. Application Data

(60) Provisional application No. 61/132,670, filed on Jun. 20, 2008, provisional application No. 60/964,250, filed on Aug. 10, 2007, provisional application No. 60/958,997, filed on Jul. 10, 2007.

(52) U.S. Cl.
CPC ... *G01N 21/6486* (2013.01); *G01N 2021/458* (2013.01); *G01N 2201/061* (2013.01); *G01N 2201/105* (2013.01); *G01N 2201/12* (2013.01)

(56) References Cited

U.S. PATENT DOCUMENTS

| | | | |
|---|---|---|---|
| 8,848,199 B2 | 9/2014 | Choi et al. | |
| 2002/0122254 A1* | 9/2002 | Gluckstad | G02B 27/46 359/559 |
| 2006/0291712 A1 | 12/2006 | Popescu et al. | |
| 2007/0058174 A1 | 3/2007 | Hill | |
| 2008/0259345 A1 | 10/2008 | Fukutake | |

OTHER PUBLICATIONS

International Search Report by the International Searching Authority for International Application PCT/US2008/008447 dated Sep. 30, 2009. (8 pages).

Mann et al., "Movies of cellular and sub-cellular motion by digital holographic microscopy", Biomedical Engineering Online, 5 (21), Mar. 23, 2006. (10 pages).

Vertu et al., "Optical projection microtomography of transparent objects," SPIE-OSA Biomedical Optics, SPIE vol. 6627, 2007.

Charriere et al., "Biological cell (pollen grain) refractive index tomography with digital holographic microscopy," Proc. of SPIE, vol. 6090, 2006.

Rangayyan et al., "Algorithms for limited-view computed tomography: an annotated bibliography and a challenge." Applied Optics, vol. 24, No. 23, Dec. 1985.

Dengler, J. "A multi-solution approach to the 3D reconstruction from an electron microscope tilt series solving the alignment problem without gold particles," Ultramicroscopy 30 (1989) 337-348.

Vishnyakov et al., "Optical tomography of living cells using phase-shifting Linnik microscope," part of the EUROPTO conference on optical microscopy, SPIE vol. 3568, Stockholm, Sweden, Sep. 1998.

Zhou et al., "Optical coherence tomography based projected index computed tomography," Fifth international conference on photonics and imaging in biology and medicine, SPIE vol. 6534, 2007.

Ikeda, T. "Hilbert phase microscopy for investigating fast dynamics in transparent systems," Optical Society of America, vol. 30, No. 10, May 2005.

Zysk et al., "Projected index computed tomography," Optical Society of America, Optics Letters, vol. 28, No. 9, May 2003.

Suhara, H. "Interferometric measurement of the refractive-index distribution in plastic lenses by use of computed tomography," Optical Society of America, Applied Optics, vol. 41, No. 25, Sep. 2002.

Charriere et al., "Living specimen tomorgraphy by digital holographic microscpy: morphometry of testate amoeba," Optics Express, vol. 14, No. 16, 2006.

Sun, P., "Spatial phase-shifting technique in large image-shearing electronic speckle pattern interferometry," Optical Engineering, vol. 46(2), Feb. 2007.

Peng et al., "3-D imaging and modeling—Part I: acquisition and registration," Optik Optics, International Journal for Light and Electron Optics, Optik 113, No. 10(22) 448-452.

Choi et al., "Extended depth of focus in tomographic phase microscopy using a propagation algorithm," Optical Society of America, Optics Letters, vol. 33, No. 2, Jan. 2008.

Choi et al., "Field-based angle-resolved light-scattering study of single live cells," Optical Society of America, Optics Letters, vol. 33, No. 14, Jul. 2008.

Choi et al., "Tomographic phase microscopy," Nature Methods, Nature Publishing Group, vol. 4, No. 9, Sep. 2007.

Lue et al., "Quantitative phase imaging of live cells using fast Fourier phase microscopy," Applied Optics, Optical Society of America, vol. 46, No. 10, Apr. 2007.

Fang-Yen et al, "Imaging voltage-dependent cell motions with heterodyne Mach-Zehnder phase microscopy," Applied Optics, Optical Society of America, vol. 32, No. 11, Jun. 2007.

Lue et al., "Tissue refractometry using Hilbert phase microscopy," Applied Optics, Optical Society of America, vol. 32, No. 24, Dec. 2007.

Choi et al., "Tomographic phase microscopy—Quantitative 3D imaging of living cells," www.eMagazineBIOforum.com.

\* cited by examiner

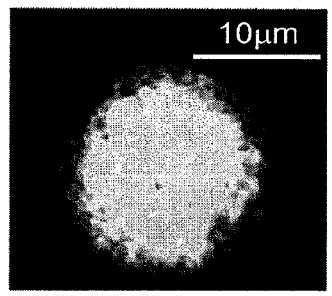
FIG. 3C
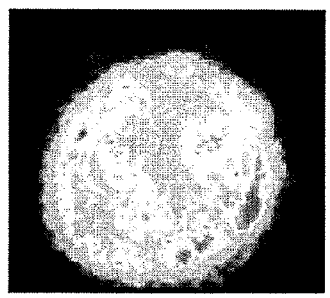
FIG. 3D
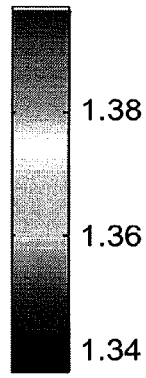
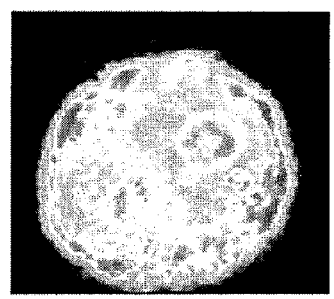
FIG. 3E
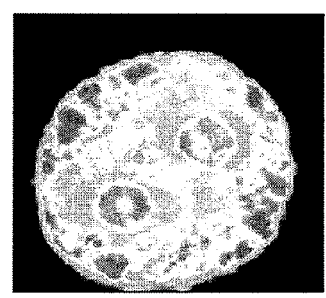
FIG. 3F
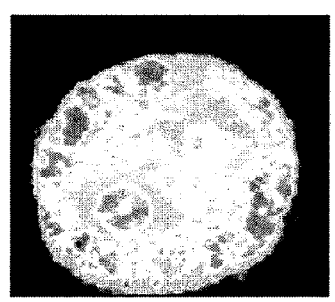
FIG. 3G
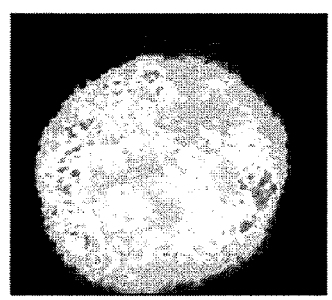
FIG. 3H
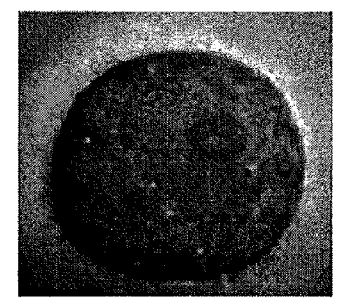
FIG. 3I
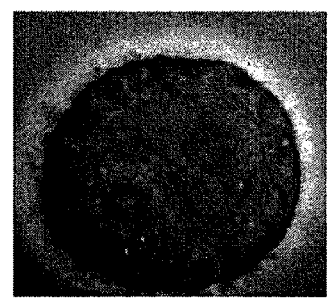
FIG. 3J

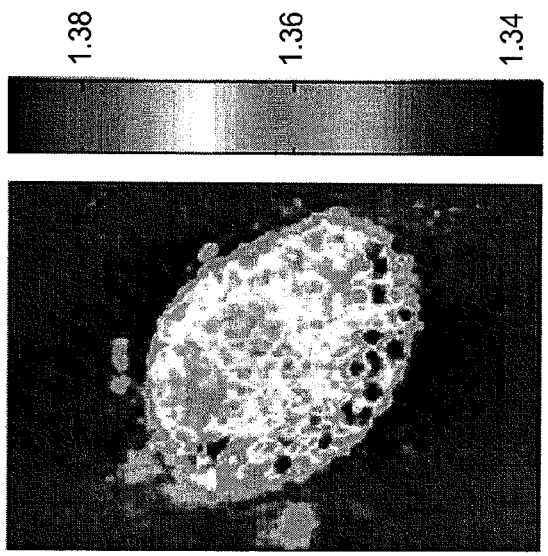
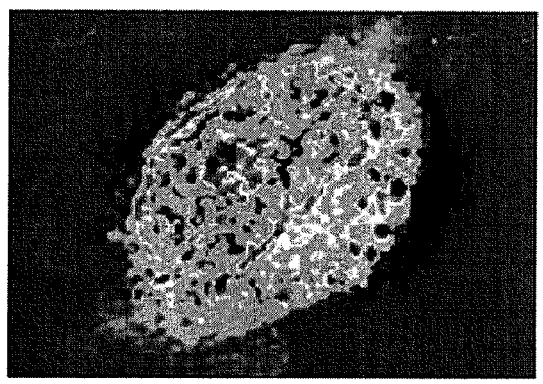
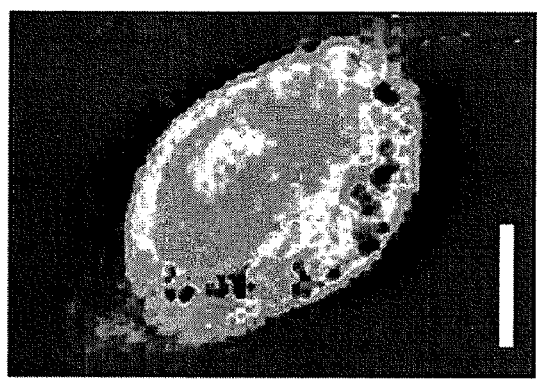
FIG. 4C
FIG. 4B
FIG. 4A

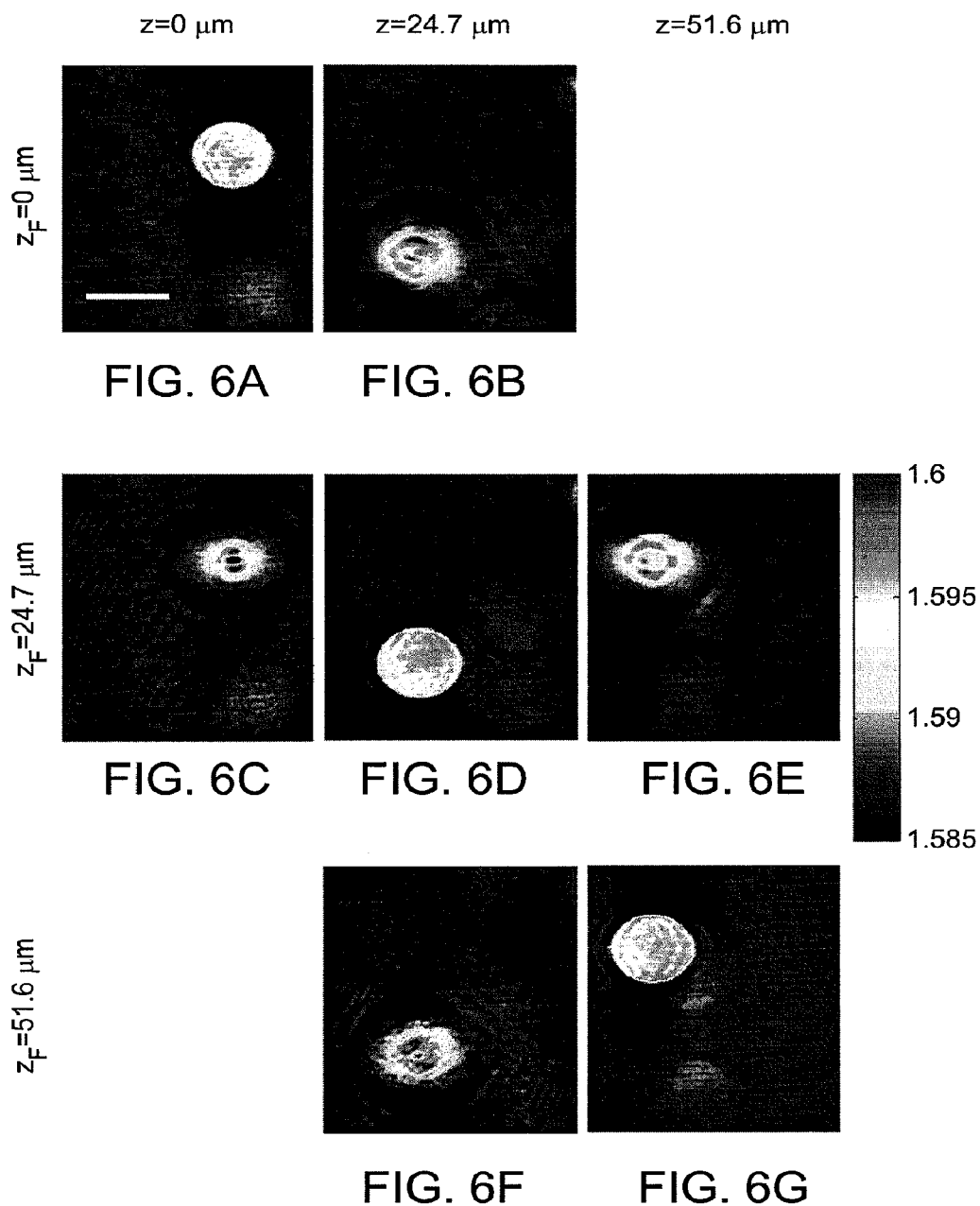

FIG. 8A
FIG. 8B
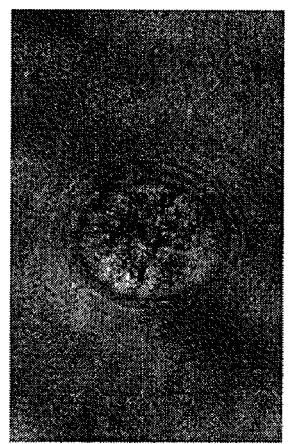
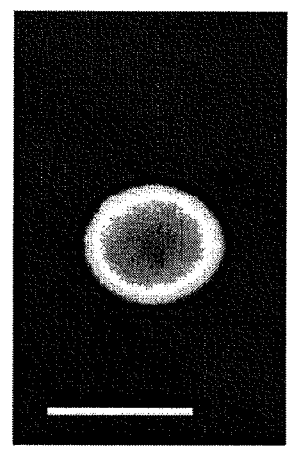
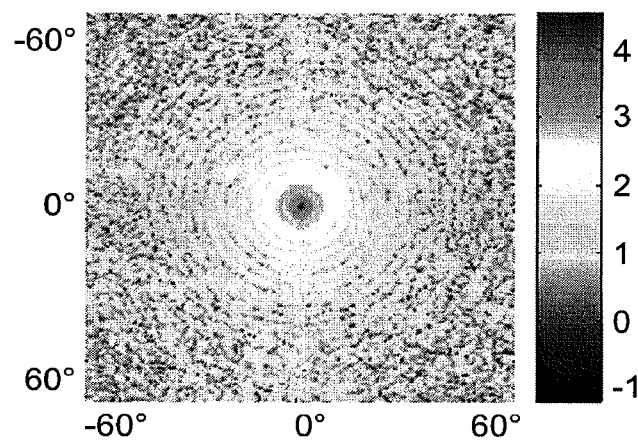
FIG. 8C

FIG. 13A    FIG. 13B
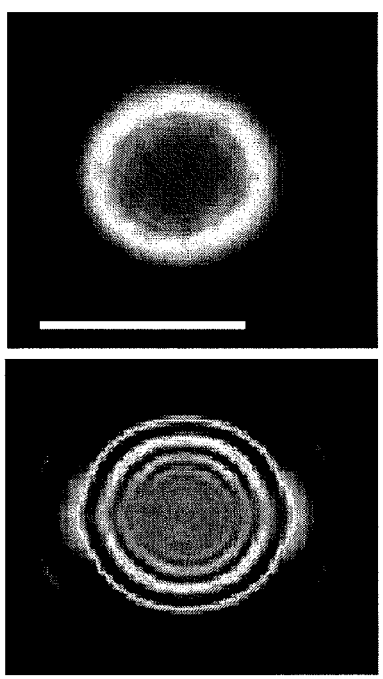
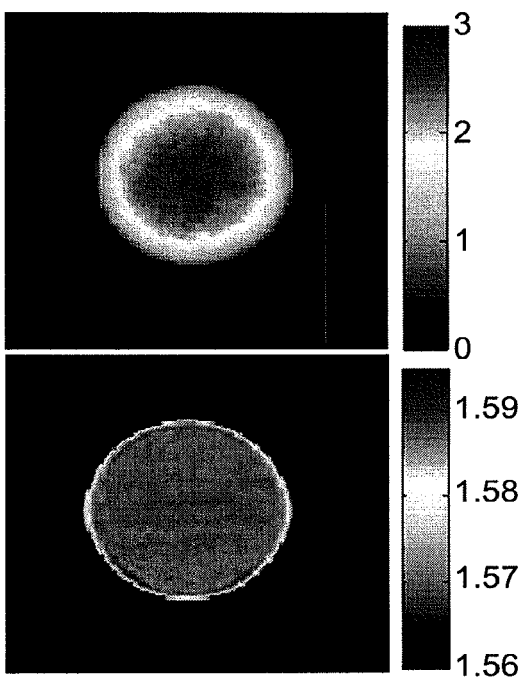
FIG. 13C    FIG. 13D

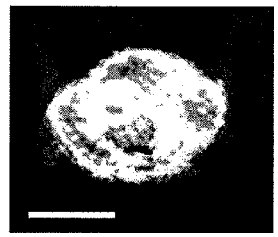
FIG. 14A
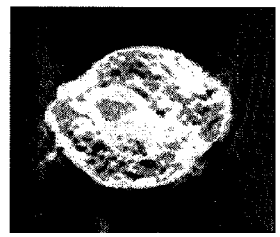
FIG. 14F
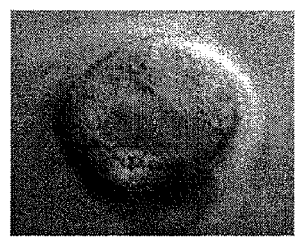
FIG. 14J
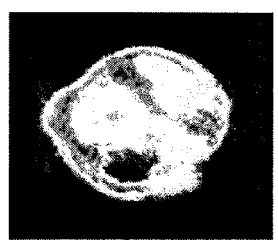
FIG. 14B
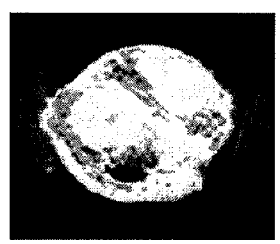
FIG. 14G
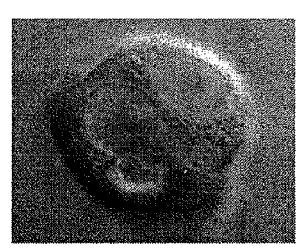
FIG. 14K
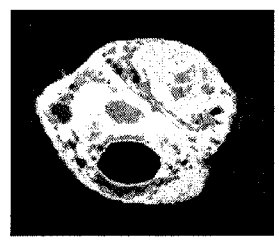
FIG. 14C
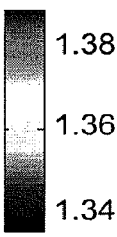
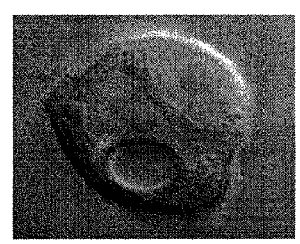
FIG. 14L
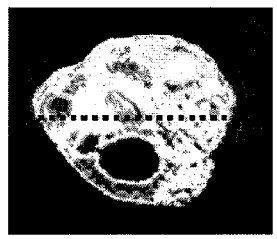
FIG. 14D
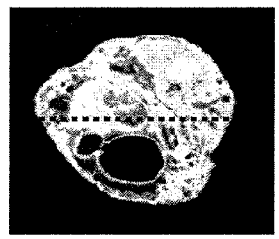
FIG. 14H
FIG. 14M
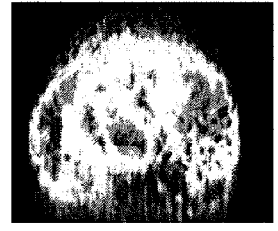
FIG. 14E
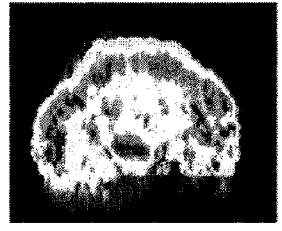
FIG. 14I

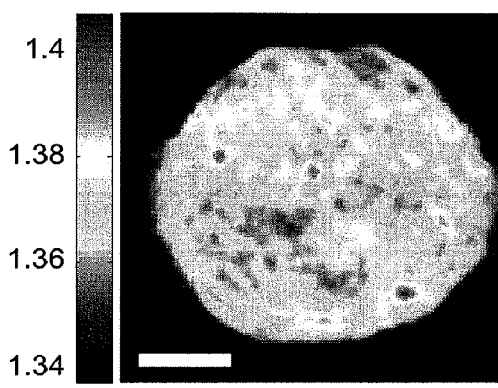 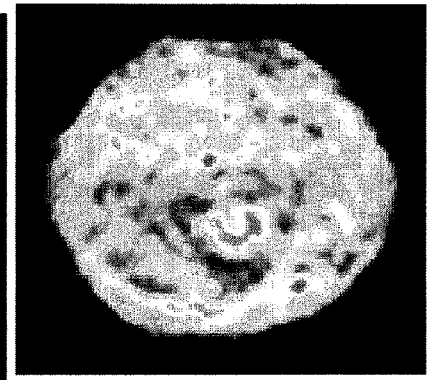
FIG. 17A     FIG. 17B
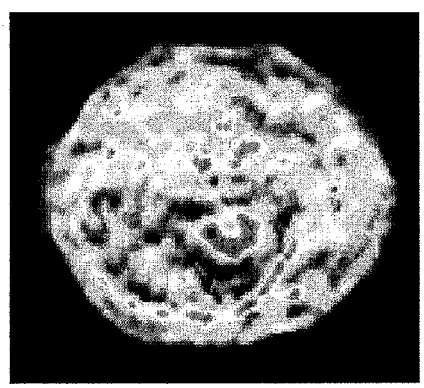 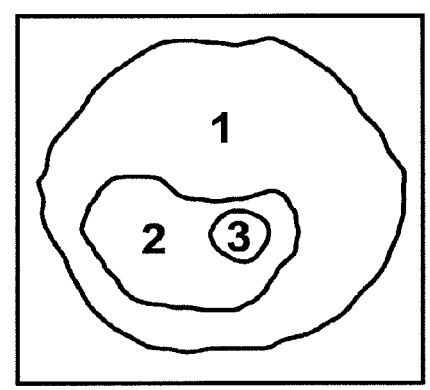
FIG. 17C     FIG. 17D

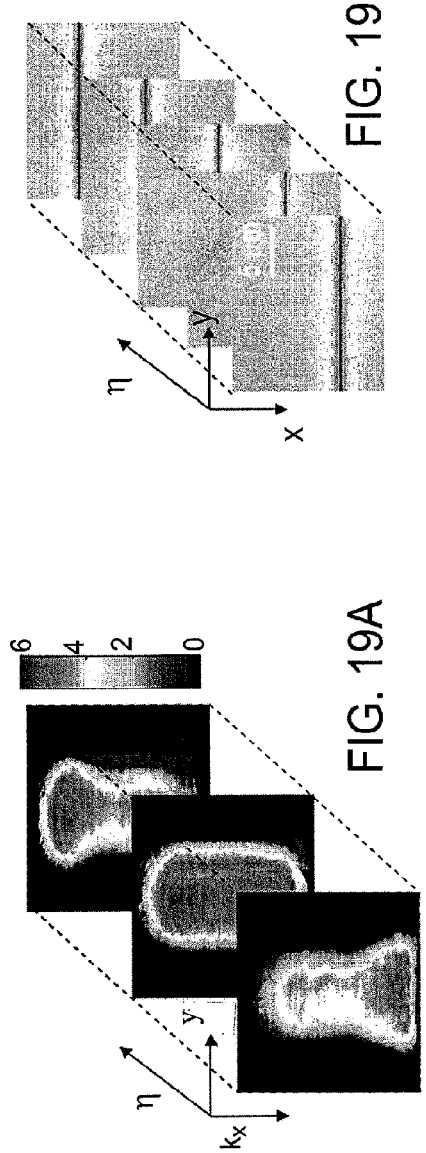
FIG. 19A
FIG. 19B
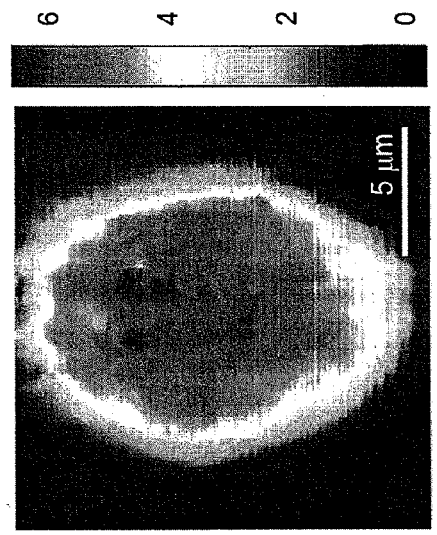
FIG. 19D
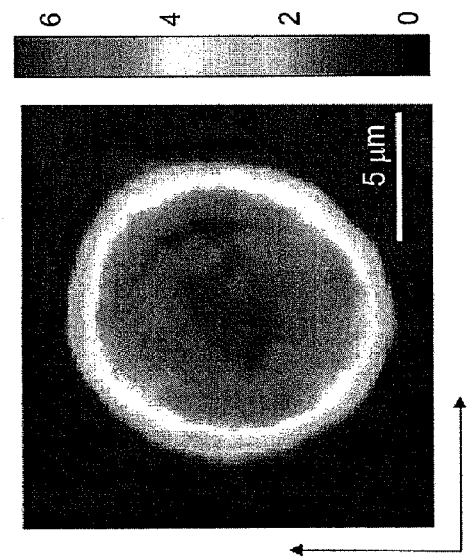
FIG. 19C

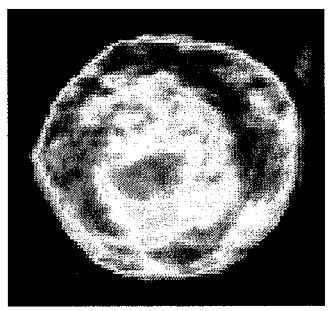
FIG. 20D
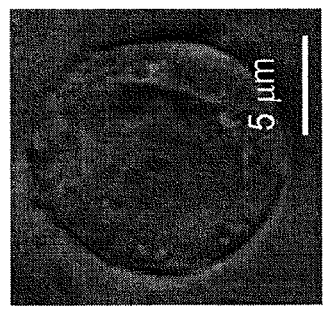
FIG. 20H
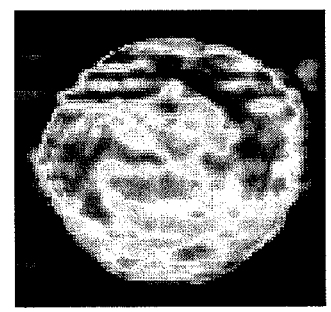
FIG. 20C
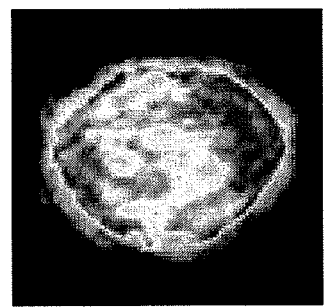
FIG. 20G
FIG. 20B
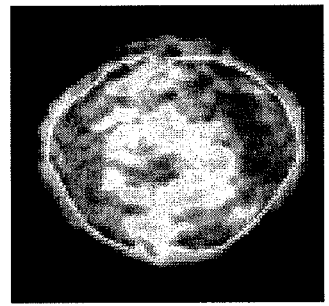
FIG. 20F
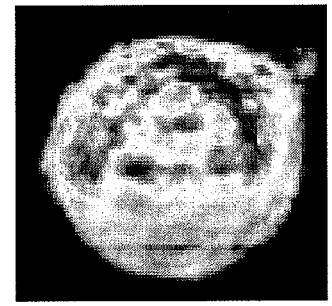
FIG. 20A
FIG. 20E

DISTRIBUTION OF REFRACTIVE INDEX MEASUREMENT BY SYNTHETIC APERTURE TOMOGRAPHY

CROSS REFERENCE TO RELATED APPLICATIONS

This application is a divisional of U.S. application Ser. No. 12/218,029 filed Jul. 10, 2008 and claims priority to U.S. Provisional Application No. 60/958,997, filed Jul. 10, 2007, U.S. Provisional Application No. 60/964,250, filed Aug. 10, 2007; and to the U.S. Provisional Application No. 61/132,670 filed Jun. 20, 2008, all entitled TOMOGRAPHIC PHASE MICROSCOPY. The entire contents each of the aforementioned patent applications is incorporated herein by reference.

STATEMENT REGARDING FEDERALLY SPONSORED RESEARCH

The invention was made with support from National Science Foundation Grant DBI-0754339 and National Institutes of Health Grant P41-RR02594-18. The United States Government has certain rights in the invention.

BACKGROUND OF THE INVENTION

High resolution light microscopy is limited not only by the diffraction properties of light but also the optical inhomogeneities of the sample. Adaptive optics and deconvolution techniques can be used to correct sample-induced aberrations if the aberrations due to the refractive index variations are adequately measured. To be most effective, however, both correction strategies require quantitative knowledge of the 3-D position-dependent refractive index of the sample.

The refractive index reveals a unique aspect of cellular structure, and is important in the measurement of cell and tissue light scattering, laser trapping of single cells, flow cytometry, total internal reflection microscopy, and generally involving the interaction of light with cells and tissues.

Prior methods for cellular index measurement typically provide the average refractive index of a cell, ignoring spatial variations due to sub-cellular structure. Moreover, they require immersion of cells in liquids of various refractive indices and subsequent observation with phase contrast microscopy. This procedure is cumbersome and is limited by the tendency of some cells to be altered by the immersion liquids, which are typically not physiologically controlled. More recently, accurate measurements of average index have been performed using quantitative phase microscopy techniques, but measurement of three-dimensional spatial variation has not been possible.

SUMMARY OF THE INVENTION

The present invention relates to the determination of refractive index distribution within a medium or material using an interferometer measurement. A preferred embodiment provides for the measurement of refractive index in a three-dimensional region or volume by scanning at a plurality of angles. The method can employ light from a source using the measurement of projections of refractive index in multiple directions.

A preferred embodiment provides quantitative, high-resolution three-dimensional refractive index measurements of biological media such as cells and multicellular organisms with no need for sample perturbation or immersion in special media. The measurements can be obtained using live cells, tissues, or organisms.

A system for measuring refractive index in accordance with the invention can use an interferometric method in which interference patterns are detected between a frequency shifted reference light and light transmitted through a region of interest from different angles.

An actuator can be used to move a scanning optical element such as a mirror to alter the angle of incidence on a biological sample such as tissue or other cellular structure. A plurality of images can be obtained that are used to determine the three-dimensional distribution of the refractive index within the sample without moving the sample or immersing the sample in an index changing material.

A preferred embodiment of the invention utilizes the immersion of the sample in a medium while altering the index of refraction by less than five percent and preferably by less than one percent.

Yet another preferred embodiment of the invention provides a tomography system for measuring a medium. The system can include a light source, a first light path coupling light from the light source onto the medium, a scanner that scans the first light path through the medium at different angles, a second light path that couples a reference light onto light transmitted through the medium, a detector that detects the reference light combined with the light transmitted through the medium, and a processor that determines a three-dimensional distribution of a refractive index of the medium from the detected light.

Still another preferred embodiment of the invention provides a spatial fringe pattern demodulation method for performing tomographic phase microscopy. The method can include scanning light along a first light path through a medium at a plurality of angles, combining the light transmitted through the medium with a reference light, detecting the combined light, and determining a phase image of the medium using spatial fringe pattern demodulation. This embodiment allows video rate acquisition of phase images of the medium, and can be used to investigate time dependent changes in a medium, including changes is size, shape, structure, or molecular organization of a cell, including responses to stimuli or chemical or biological agents.

Another preferred embodiment of the invention provides a tomography system for measuring a medium using spatial fringe pattern demodulation. The system can include a light source, a first light path coupling light from the light source onto the medium, a scanner that scans the first light path through the medium at different angles, a second light path that couples a reference light onto light transmitted through the medium, a detector that detects the reference light combined with the light transmitted through the medium, and a processor that determines a phase image of the medium from the detected light using spatial fringe pattern demodulation.

A preferred embodiment of the invention provides a synthetic aperture method for measuring the refractive index of a medium. The method can include transmitting a focused beam of light along a first light path through a medium, combining the light transmitted through the medium with a reference light detecting the combined light determining a phase image and an amplitude image of the medium combining the phase and amplitude images to form an electrical field image of the medium, and determining the distribution of a refractive index of the medium using synthetic aperture analysis. The method is well suited for situations where the medium or a sample within the medium is in translational motion. For a medium in motion, a series of refractive index distributions of the medium are formed, from which a refractive index distribution of the medium itself can be determined.

Still another embodiment of the invention provides a tomography system for measuring a translocating medium. The system can include a light source, a first light path coupling focused light from the light source onto the medium, a second light path that couples a reference light onto light transmitted through the medium, a detector that detects the reference light combined with the light transmitted through the medium, and a processor that determines a refractive index distribution of the medium from the detected light using synthetic aperture analysis.

Yet another preferred embodiment of the invention provides systems and methods for the diagnosis of disease such as cancerous or precancerous tissue. By quantitative measurement of the refractive index and other physical characteristics of tissue, such as cell size and distribution, methods and systems according to the invention, such as those described above, can provide important diagnostic information on biopsied tissue samples.

DESCRIPTION OF THE DRAWINGS

FIGS. 3A-3J are refractive index tomograms in which the dotted box is a cube of side 20 microns and FIGS. 3C-3H are slices of the tomogram. FIGS. 3I and 3J are bright field images taken at the same focus as FIG. 3E-F for comparison.

FIGS. 4A-4C are slices of a cell in normal culture medium (4A), after 3 minutes in a medium with 0.38% acetic acid (4B), and 3 minutes after replacing the original medium without acetic acid (4C), respectively.

FIGS. 5A-5E illustrate a sample geometry and both projection phase images (B,C) and refractive index tomogram (D,E) of beads in suspension.

FIGS. 6A-6G are tomographic images of beads in suspension.

FIGS. 8A-8C are amplitude images of the bead, a quantitative phase image thereof, and angular scattering map.

FIGS. 13A-13D illustrate the effect of sampling depth on refractive index tomograms; FIG. 13A shows a phase image of a 10 μm polystyrene bead with the focus 4 μm above the center of the bead; FIG. 13B shows a quantitative phase image after applying the propagation correction, with the focus brought to the center of the bead and the color bar indicates phase in radians; FIG. 13C is an x-y slice of the refractive index tomogram for the focus the same as in 13A; FIG. 13D is an x-y slice of the refractive index tomogram after applying the propagation algorithm. The color bar indicates the refractive index measured at $\lambda=633$ nm.

FIGS. 14A-14M show refractive index tomogram analysis of an HT-29 cell before and after applying the propagation correction. FIGS. 14A-14D show successive x-y slices of the refractive index tomogram at 2 μm intervals in the axial direction before applying the propagation correction. FIGS. 14F-14H show x-y slices corresponding to FIGS. 14A, 14B and 14C after applying the propagation correction. FIGS. 14E and 14I represent x-z slices along the dashed lines indicated in 14D and 14H, respectively, and the color bar indicates refractive index at $\lambda=633$ nm. FIGS. 14J-14M are bright field images with the image focus corresponding to FIGS. 14A-14D; the scale bar is 10 μm.

FIG. 16A shows the vectors for the reference beam ($k_R$) and the sample beam ($k_S$). FIGS. 16B-D show raw images of the bead at $\theta=-\theta_{max}$, 0, and $+\theta_{max}$, respectively. FIGS. 16E-G show the phase images corresponding to FIGS. B-D, respectively.

FIGS. 17A-F show results obtained from video rate refractive index tomograms of a HeLa cell during exposure to acetic acid solution at times t=0 (FIG. 17A), t=1.3 s (FIG. 17B), and t=2.6 (FIG. 17C). Scale bar=5 microns. FIG. 17D depicts regions of interest in the HeLa cell image. FIG. 17E shows the average refractive index of each area of interest from FIG. 17D as a function of time after acetic acid addition. FIG. 17F shows the standard deviation of the refractive index for each area of interest.

FIGS. 18A and 18B depict the experimental set up. FIG. 18C is a bright field image of a 10 micron polystyrene bead. FIG. 18D shows a line focus beam positioned at the center of the bead. FIG. 18E shows a set of four interferogram phase images. FIG. 18F shows a reconstructed phase image of a moving 10 micron polystyrene bead.

FIGS. 19A-D show a HeLa cell imaged during translocation using synthetic aperture tomography. 19A shows a set of phase images as a function of cell translocation. 19B shows a series of amplitude images as a function of cell translocation. 19C and 19D show phase images of the HeLa cell at zero and 35 degrees, respectively.

FIGS. 20A-H present a HeLa cell imaged by synthetic aperture tomography. FIGS. 20A-G show x-y slices of a reconstructed tomogram, with 1 micron axial distance between slices. FIG. 20H is a bright field image of the same cell.

DETAILED DESCRIPTION OF THE INVENTION

Figure 1:
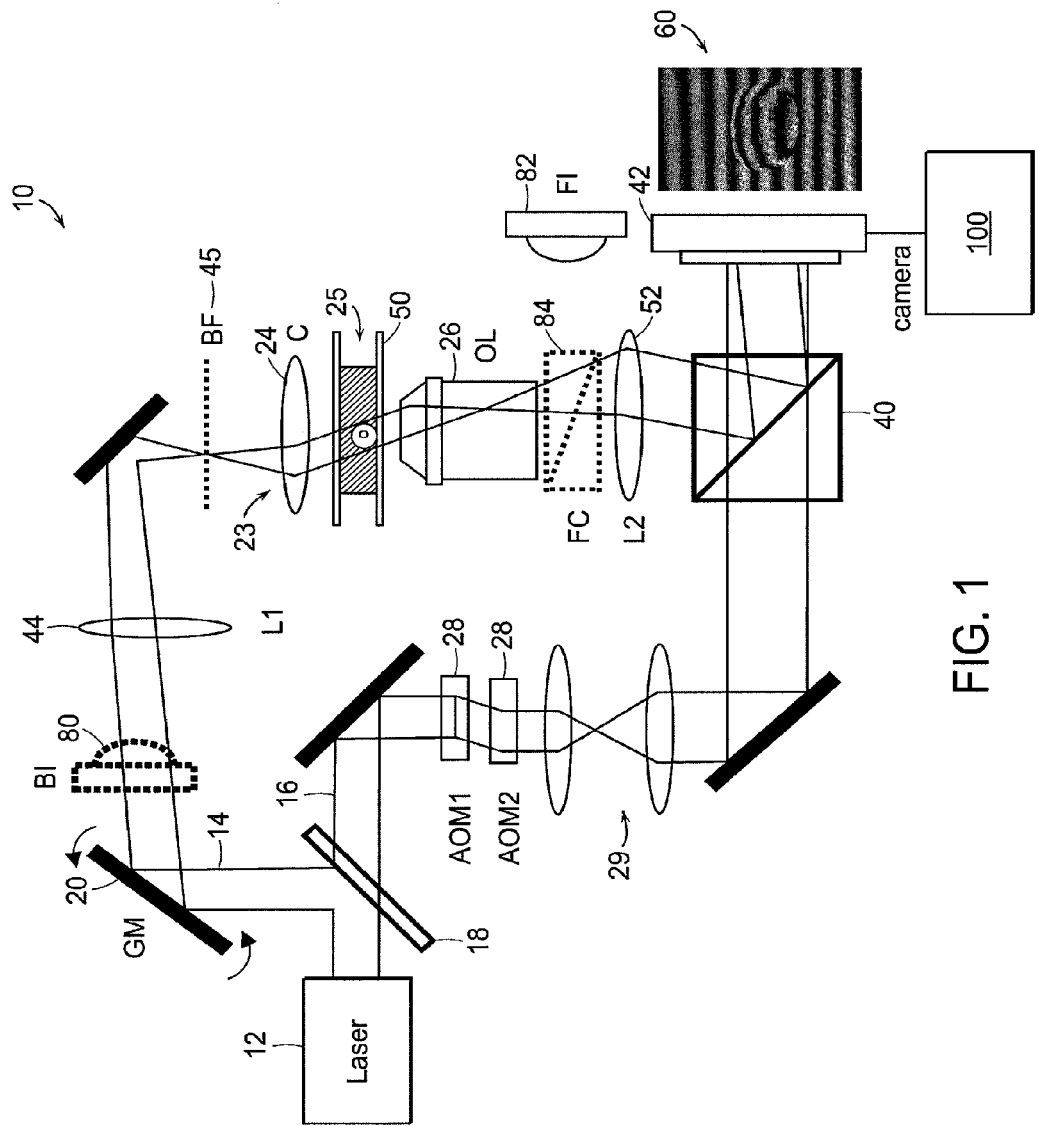
FIG. 1 illustrates a system for measuring the three-dimensional distribution of the refractive index of an object.

The system 10 for performing measurements is illustrated in FIG. 1 and is based on a Mach-Zehnder heterodyne interferometer, which provides quantitative phase images from time-dependent interference patterns induced by the frequency shifting of a reference beam relative to the sample beam. A light source 12 such as a helium-neon laser beam ($\lambda=633$ nm) is divided into measurement 14 and reference arm 16 paths by a beamsplitter 18. An actuator 20, such as a galvanometer-mounted tilting mirror, is used to vary the angle of illumination 23 of the medium 25 being measured, which is positioned between the oil-immersion condenser 24 and objective lenses 26. In the reference arm, the laser beam passes through two acousto-optic modulators 28 (AOMs) which shift the frequency of the laser beam by 1250 Hz. A beamsplitter 40 recombines the sample and reference laser beams, forming an interference pattern 60 at the image plane. For each angle of illumination a detector 42 such as a CMOS camera (Photron 1024PCI) records a plurality of images on memory of computer 100, for example, 4 images at 5000 frames per second, such that the sample-reference phase shift between consecutive frames is $\pi/2$. Phase images are then calculated by applying phase shifting interferometry. A processor in computer 100 is programmed to determine the three-dimensional distribution of the refractive index in the medium.

In the interferometer sample arm, the beam is incident on a tilting mirror controlled by a galvanometer such as the HS-15 provided by Nutfield Technology. A lens 44 (f=250 mm) is used to focus the beam at the back focal plane 45 of the oil-immersion condenser lens 24 (Nikon 1.4NA), which recollimates the beam to a diameter of approximately 600 µm. The distances from tilting mirror to the lens 44 and from the lens 44 to the back focal plane 45 of the condenser lens are set equal to the focal length of the lens 44 such that the tilting mirror is conjugate to the sample plane.

The biological media can be prepared in a chamber 50 composed of two glass coverslips separated by a plastic spacer ring and partially sealed with adhesive. Light transmitted through the sample is collected by an infinity-corrected, oil-immersion objective lens (Olympus UPL-SAPO 100XO, 1.4 NA). A tube lens 52 (f=200 mm) focuses an image of the sample onto the camera plane with magnification M=110.

In the reference arm or beam path, the laser beam passes through two acousto-optic modulators 28(AOMs) (Isomet) driven at frequencies $\omega_1$=110.1250 MHz and $\omega_2$=110.0000 MHz, respectively, using a digitally synthesized RF driver to modulate the reference light frequency. Irises select the +1 and −1 order beams, respectively, such that the total reference beam frequency shift is 1250 Hz. After passing through the AOMs, the reference beam is spatially filtered and enlarged by a beam expander 29. The focus and tilt of sample and reference beams are adjusted to minimize the difference between the two wavefronts.

For each phase image, a high speed CMOS camera (Photron 1024-PCI, 17 µm pixel size) records 4 images separated by 200 µs, exactly one-quarter the reciprocal of the heterodyne frequency. In this way, four interference patterns $I_1, I_2, I_3, I_4$ are recorded in which the sample-reference phase shift between consecutive images differs by $\pi/2$. Phase images are then obtained by applying phase shifting interferometry using the four-bucket algorithm $\phi(x,y)=\arg(((I_4-I_2)+i(I_3-I_1)))$. $2\pi$-phase ambiguities are resolved by phase unwrapping using Goldstein's algorithm. The fast acquisition time between frames reduces the effects of external noise. Exposure times are typically ~20 µs. By stepping the galvanometer mirror, 81 phase images are recorded for sample illumination angles $\theta$=−60 to +60 degrees in steps of 1.5 degrees.

Figure 2A:
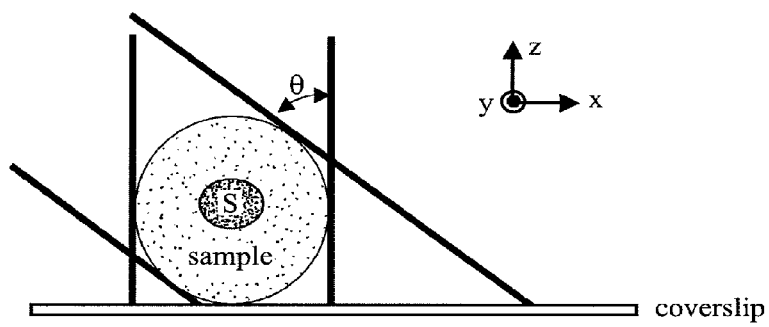
FIGS. 2A-2E illustrate an illumination geometry, projection phase line profiles at θ=0 and 45 degrees, and corresponding projection phase images, respectively.
Figure 2B:
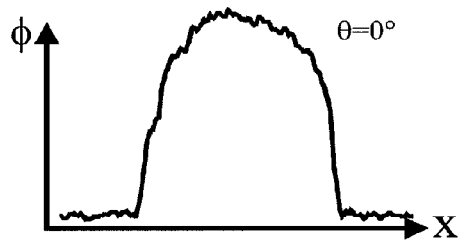
Figure 2C:
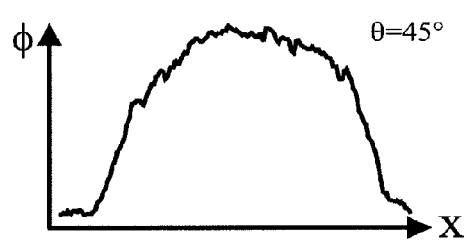
Figure 2D:
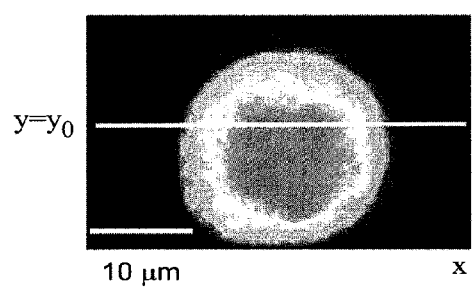

The phase projection geometry is illustrated schematically in FIG. 2A. Data from a single HeLa cell in a culture medium (DMEM with 10% fetal bovine serum) were obtained. The phase image of the cell for $\theta$=0 degree is shown in FIG. 2D. For nonzero $\theta$ the image displays a background fringe pattern due to the tilt between sample and reference beams, with fringe spacing $d=\lambda M/(\lambda \sin \theta)$, with M=110 the magnification and n the index of the sample medium (image 60 next to the camera in FIG. 1). The corresponding phase image shows a $2\pi$ jump at every fringe. After unwrapping the phase, the phase image appears as a nearly linear phase ramp with the phase profile of the cell almost indistinguishable.

Figure 2E:
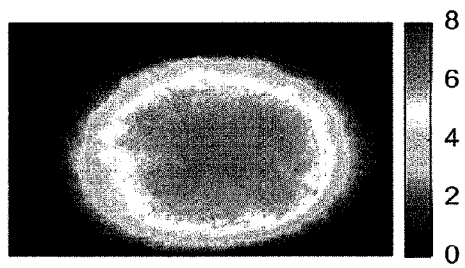

The phase image at an illumination angle of 45° is shown in FIG. 2E after phase unwrapping and subtraction of the background phase ramp via a least-square linear fit to a portion of the field of view with no sample. Compared to the zero degree angle case seen in FIG. 2B, the line profile of the phase image is elongated at nonzero illumination, as seen in FIG. 2E, because the phase measurements are performed in an image plane parallel to the sample substrate, regardless of incident beam direction.

A similar angle-dependent set of phase images is obtained with no sample present, and the resulting set of background phase images is subtracted from the sample phase images to eliminate residual fixed-pattern phase noise due to optical aberrations and imperfect alignment.

For near-plane wave illumination of a thin sample with small index contrast, the phase of the transmitted field is, to a good approximation, equal to the line integral of the refractive index along the path of beam propagation. Therefore, the phase image can simply be interpreted as the projection of refractive index or a tomographic image as shown in FIG. 2A.

To reconstruct a 3-D refractive index tomogram from the projection phase images, a procedure based on a filtered back-projection method is used to provide a three-dimensional representation of the refractive index in the region of interest. A discrete inverse Radon transform can be applied to every X-$\theta$ slice in the beam rotation direction, with X the coordinate in the tilt direction. To compensate for the angle between imaging and illumination directions, divide the X values by cos $\theta$. Illumination angles are limited to $|\theta|<60$ degrees by the numerical aperture of condenser and objective lenses. To reduce the effects of the missing projections, an iterative constraint method can be used as described hereinafter.

The limitation of projection angles to $|\theta|<60$ degrees poses a problem of missing information. To reduce the effect of the missing projections, an iteration based constraint method can be used. In this method, the reconstruction is first performed by filling missing-angle projections with values of zero. The resulting reconstructed image, which represents the difference of the refractive index relative to that of the surrounding medium, is constrained to contain only non-negative values and set to zero outside some boundary chosen well outside the margins of the cell. Next, a $\theta$-dependent projection of this reconstruction is calculated and constrained to equal experimentally measured projections over the range of measured angles $\theta$. The process is repeated 10-15 times to ensure convergence.

Since all phase measurements can be measured relative to other points in the field of view, the tomographic data from the method gives the refractive index relative to that of the medium. The absolute index was calculated by adding the relative index to the index of refraction of the culture medium, found to be 1.337 using a different standard interferometric method.

Methods of the invention can include a reference measurement in which refractive index tomograms of 10 µm polystyrene beads (Polysciences #17136, n=1.588 at $\pi$=633 nm) immersed in oil with a slightly smaller refractive index (Cargille #18095, n=1.559 at $\pi$=633 nm). Tomograms showed a constant refractive index inside each bead, and the refractive index difference between the bead and its surroundings was Δn=0.0285±0.0005, in agreement with the manufacturers' specifications for beads and oil (Δn=0.029). Similar measurements with a range of oil refractive indices from n=1.55 to n=1.59 confirmed the accuracy of this measurement. By measuring the width (FWHM) of the derivative of line profiles of refractive index normal to the boundary of the sphere, the spatial resolution of this tomographic method can be estimated to be approximately 0.5 μm in the transverse (x-y) directions and 0.75 μm in the longitudinal (z) direction.

Figure 3A:
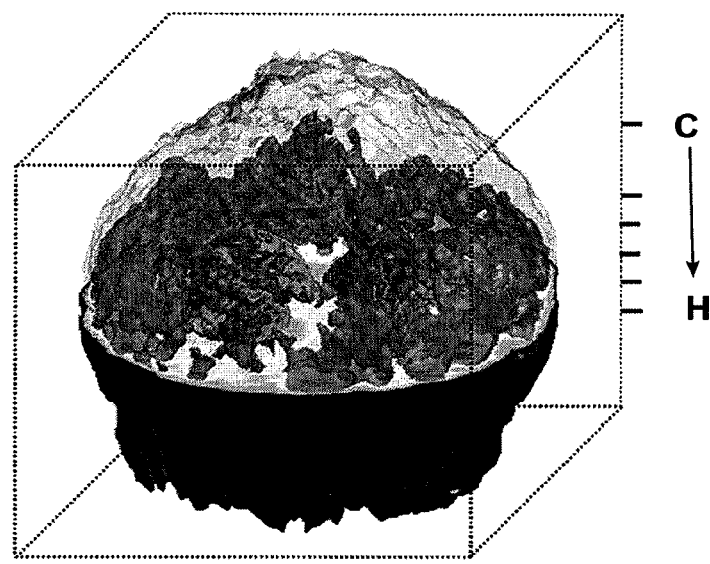
Figure 3B:
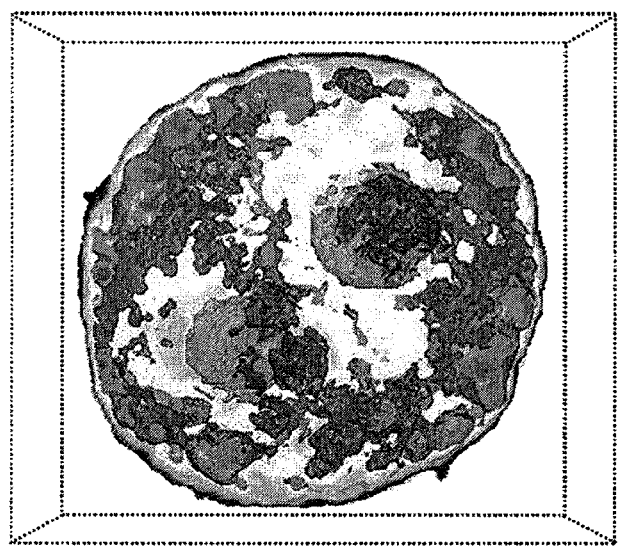

A preferred embodiment of the invention provides a method for measuring a cell. In one example, single HeLa cells in culture medium were imaged. Cells were dissociated from culture dishes and allowed to partially attach to the coverslip substrate. A 3-D index tomogram for a single cell is shown in FIGS. 3A and 3B and x-y tomographic slices of the same cell at heights of z=12, 9.5, 8.5, 7.5, 6.5 and 5.5 microns above the substrate (FIGS. 3C-3H) show that the index of refraction is highly inhomogeneous, varying from 1.36 to 1.40. Bright field images for objective focus corresponding to FIGS. 3E-3F are shown in FIGS. 3I-3J, respectively. There is a clear correspondence between the tomographic and bright field images in terms of cell boundary, nuclear boundary, and size and shape of the nucleoli. Note that the refractive index of the nucleus (n≈4.36), apart from the nucleolus, is smaller than some parts of the cytoplasm (n≈4.36-1.39) and that the refractive index of the nucleoli, n≈4.38, is larger than that of the rest of the nucleus. This is contrary to the widely cited assertion that the refractive index of the nucleus as a whole is higher than that of the rest of the cell. Similar results were obtained for cultured HEK 293 cells, B35 neuroblastoma cells, and primary rat hippocampal neurons. All cells imaged contained many small cytoplasmic particles with high refractive index, which can be lipid droplets, lysosomes, vacuoles, or other organelles.

Whitening of areas of the cervix due to topically applied acetic acid is widely used to identify suspicious sites of precancerous lesions. It has been suggested that coagulation of nucleus protein may increase the refractive index contrast between the nucleus and the cytoplasm. To measure the effect of low concentrations of acetic acid on the structure of a cell and elucidate the mechanism of acetic whitening, a preferred embodiment of methods of the invention provides for use of the tomographic microscope to record index tomograms of HeLa cells after changing the cell environment from normal culture medium, as shown in FIG. 4A, to culture medium containing 0.38% acetic acid shown in FIG. 4B. Tomograms can be obtained in less than 10 seconds, allowing measurements of relatively rapid changes in cell structure due to external perturbations. The refractive index of the nucleolus increased from 1.36 to 1.39 and the heterogeneity of the rest of the nucleus substantially increased. This indicates that the increased scattering associated with acetal whitening results from both increased refractive index contrast between nucleoli and the rest of the cell and increased inhomogeneity of refractive index throughout the cell. Three minutes after replacing the acetic acid medium with normal culture medium, the spatial variation and refractive index of nucleolus decreased somewhat but remained larger than the baseline value as shown in FIG. 4C.

Figure 4D:
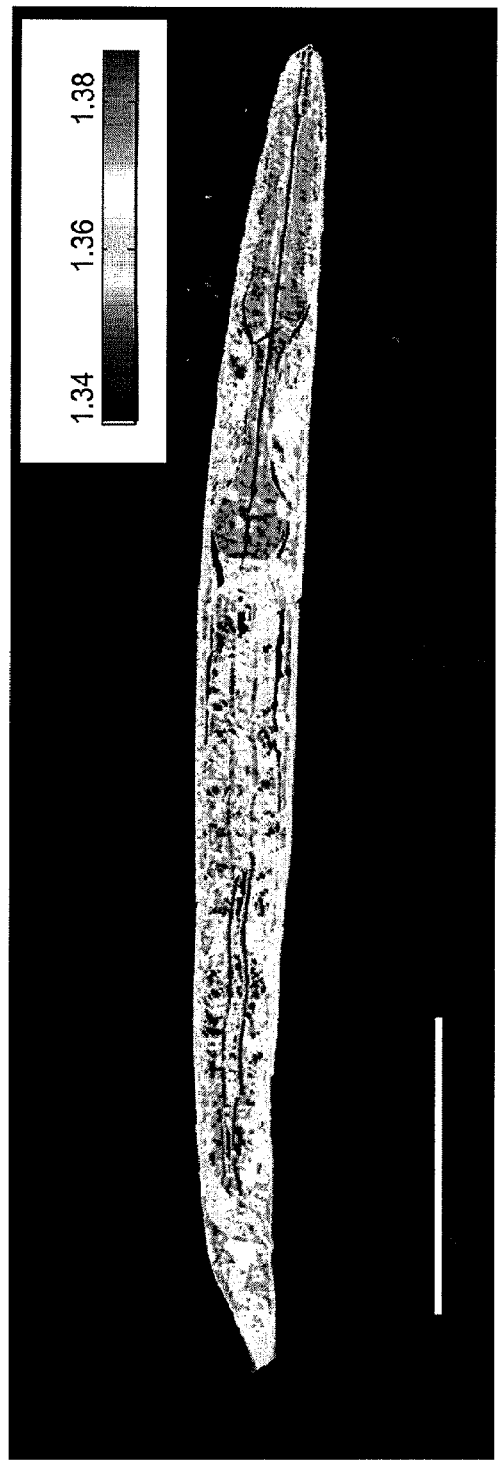
FIG. 4D is a mosaic of slices of nematode *C. elegans* with the bar indicating a refractive index at $\lambda=633$ nm.

A preferred embodiment of the invention provides for tomographic imaging of a multicellular organism, such as nematode C. elegans. Worms were paralyzed with 10 mM sodium azide in NOM buffer and imaged in the same solution. Overlapping tomograms were created and the resulting data assembled into a mosaic as shown in FIG. 4D. Several internal structures are visible, including a prominent pharynx and digestive tract.

Another preferred embodiment of the invention provides for the imaging of thick sample by obtaining refractive index tomograms from phantoms composed of polystyrene beads suspended in optical adhesive. For these samples, the projection approximation is no longer valid, as evidenced by the severely distorted images of out-of-focus beads as shown in FIGS. 5A-5G. However, by varying the objective focus, it is possible to obtain an accurate tomogram at any depth in the sample. A 3-D tomogram of a thick sample can then be obtained via a mosaic of tomograms focused at different depths.

The measurement of 3-D refractive index provides quantitative characterization of sample-induced aberrations. Such aberrations become progressively more severe for thicker tissues, although recent work has shown that biological structures ~30 μm thick can induce significant optical aberrations. We therefore explored methods for imaging samples much thicker than single cell layers.

The reconstruction algorithm approximates the phase of the sample field as the integral of refractive index along a straight line in the direction of beam propagation. This is referred to as the projection approximation; it is also known as the eikonal or ray approximation. The projection approximation places constraints not only on the index variations of the sample but also its thickness. For plane wave illumination of a typical cell, the projection approximation is accurate to depths of roughly 15 microns. To address this limitation, focusing at multiple planes has been used to extend the range of tomographic imaging.

Figure 5A:
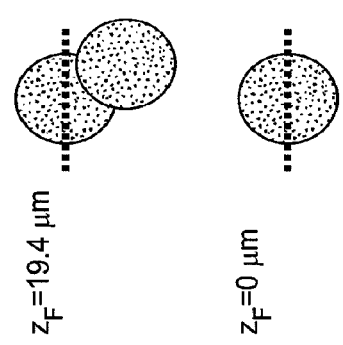

A reference measurement can be made using samples composed of 10 μm polystyrene beads (Poly sciences) suspended in UV-curable optical adhesive (Norland or Dymax) and sandwiched between two glass coverslips (FIG. 5A). Projection phase images at three different angles of illumination (−35°, 0° and 35°) for two different positions of the objective focus ($Z_F$=0 μm and $Z_F$=19.4 μm) are shown in FIGS. 5B-5C. In FIG. 5C, the in-focus bead (white arrow) is clearly resolved and satisfies the projection approximation while the out-of-focus beads exhibit ring patterns due to diffraction, demonstrating the breakdown of the projection approximation. Note that for both focus positions, in-focus beads (white arrows) are stationary with respect to change in illumination angle, while out-of-focus beads are not. This angle-dependent position information is the basis of depth discrimination in our tomographic reconstruction algorithm; the in-focus beads are separated in height from the defocused beads although all beads are present in the phase images.

Figure 5D:
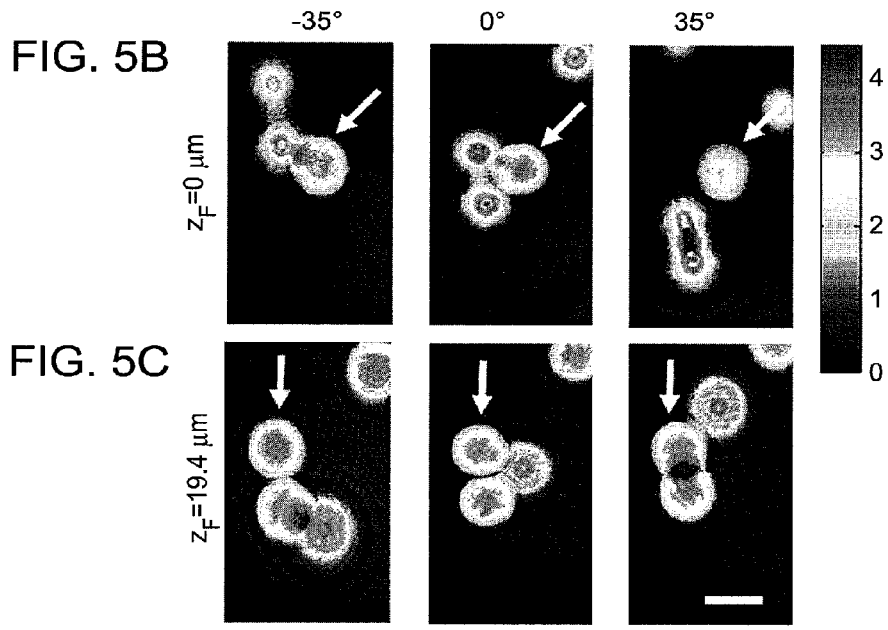
Figure 5E:
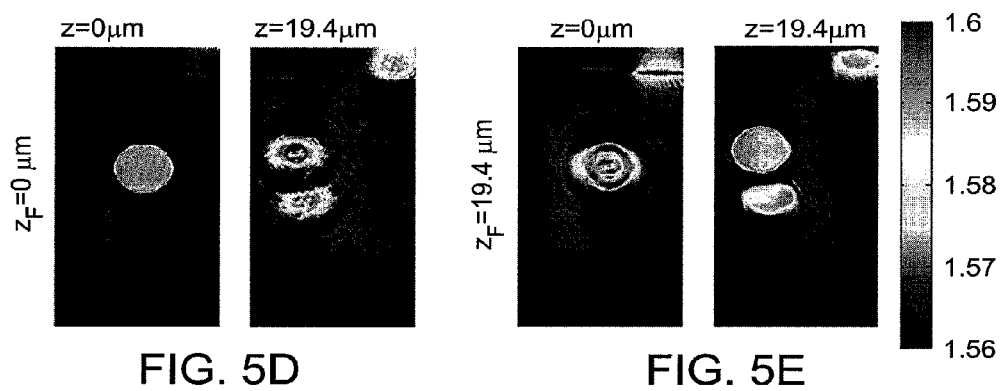

In FIG. 5D, x-y slices of the resulting tomogram at the centers of an in-focus bead (z=0 μm) and defocused bead (z=19.4 μm) are shown at an objective focus $Z_F$=0 μm. The same slices for $Z_F$=19.4 μm are shown in FIG. 5E. The in-focus beads, which satisfy the projection approximation in the phase images, are clearly resolved in the tomograms, while out-of-focus beads are blurred and exhibit ring pattern artifacts. Similar results are obtained in test samples up to 80 μm thick. In FIG. 6, three focal depths are used to measure tomograms centered at three beads, with a 51 μm separation between the highest and lowest. The signal-to-noise ratio is somewhat lower in this data, due to the smaller refractive index contrast between beads and adhesive.

This indicates a method for measuring samples of extended thickness, in which the objective focus is automatically scanned over intervals of 15 μm (or less) to cover the sample depth and obtain a set of tomograms at each step of the focus. By combining in-focus slices in series, a mosaic tomogram covering the entire sample can then be created. The maximum thickness of samples is then limited not by the projection approximation but by other factors, such as sample absorption, light scattering and the objective working distance.

A purpose of light scattering measurements of cells is to identify the size distribution of the organelles, especially the nucleus, since changes in these can be precursors of neoplastic progression. Light scattering methods can be used to determine the size distribution of intracellular organelles. In extracting the size distribution from the light scattering spectrum, prior methods modeled the shape and refractive index of cell bodies and organelles, and fitted measured angular light scattering spectrum to the predicted spectrum based on such cell models. This approach can be susceptible to the data analysis methods and the validity of the assumptions. For the sake of simplicity, most of the prior methods assumed the shape of the structures to be spheres, an approximation that is subject to error. Moreover, they also used values of refractive indices from separate studies and measurements, not from direct measurement of the cells being measured. Considering the variations of live cells even of the same type, these values may be in error. They also collected scattered light from a large number of cells, and therefore could only obtain average spectra. Cell organelles are distributed in size and refractive index and so features of individual cells may not clearly appear to the averaged angular spectra.

A preferred embodiment of the present invention provides systems and methods for measuring the 3D map of refractive index of a biological medium such as a single cell, and also to measure the light scattering spectrum from the same cell. The present invention further addresses the difficulties in measuring an angular light scattering spectrum from a single cell, due to the small signal size.

To measure the light scattering spectrum of live cells, a field-based imaging method can be used at the image plane and a Fourier transform used on the detected image to obtain the angular scattering map, which has the sensitivity to measure light scattering from a single cell. To obtain structural details of the cells or tissues, the tomographic phase microscopy method described herein can be used to map the 3D refractive index of live cells and tissues. Since the absorption of the cells under visible light illumination is negligible, the 3D map of the refractive index determines the distribution of the light scattering spectrum. The angular light scattering spectrum can be determined using the 3D refractive index distributions and the results can be compared with the spectrum obtained from field-based imaging. This can indicate how the cellular sub-structure determines the angular light scattering spectrum.

Figure 7:
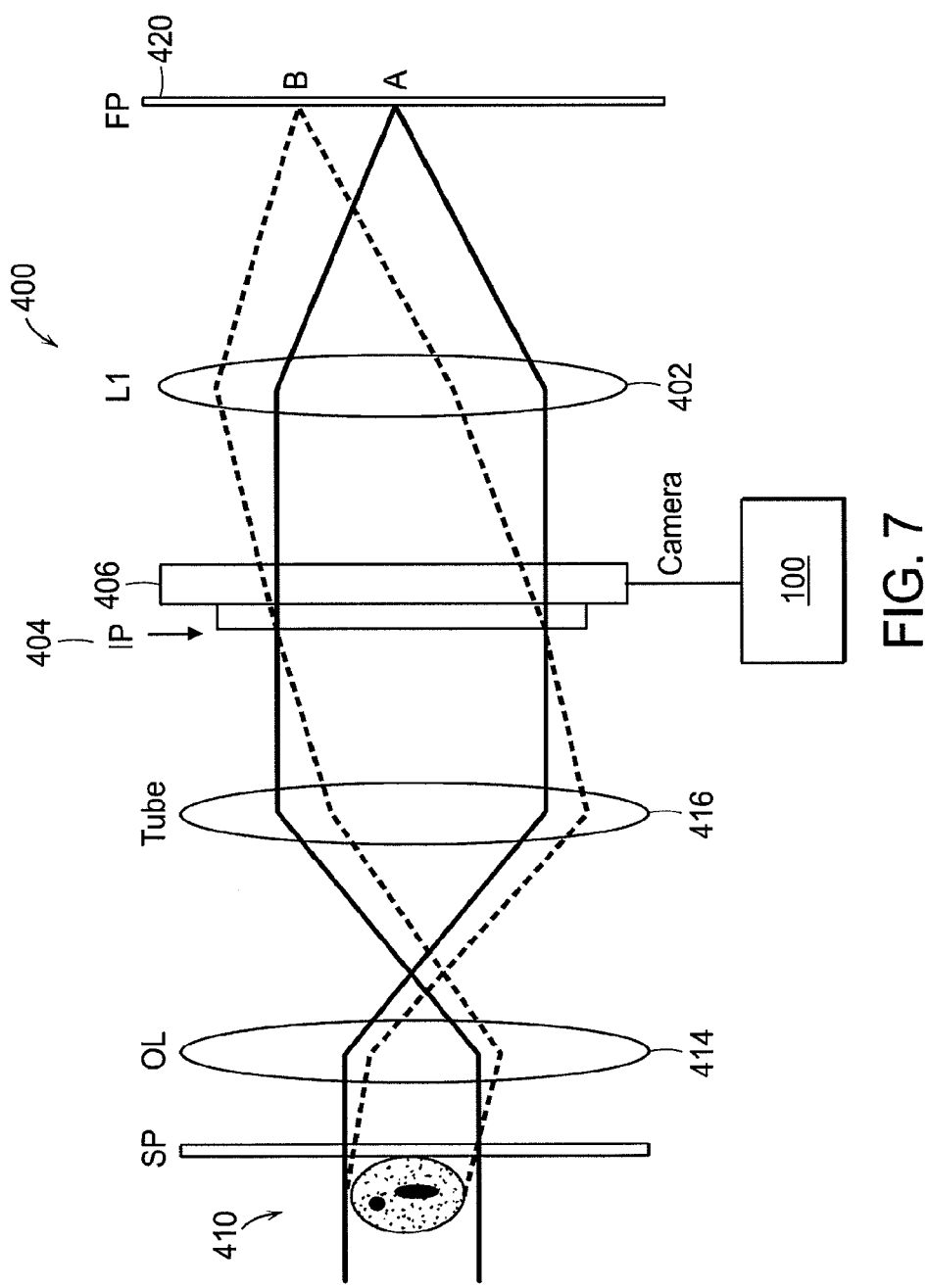
FIG. 7 is a system for measuring a scattering spectrum in accordance with the invention.

Angular light scattering is usually measured at the Fourier plane 420 of the sample as shown in the system 400 of FIG. 7. In case of a single cell 410 or a small number of cells, there is very little of high angle scattering, and most of the scattering is located near the unscattered spot (A). This makes the dynamic range in signal extremely high and requires extensive averaging to enable the detector to cover the full dynamic range. In a preferred embodiment, instead of using a Fourier lens 402 to make a scattering map, the transmitted field through lenses 414, 416 can be measured at the image plane 404 by placing the detector 406 at the image plane, with Fourier transform of the measured field being performed using software on the computer 100. The intensity distribution in the image plane is quite even for a single cell, since most cells are transparent at visible wavelengths. Therefore, the dynamic range of the signal is quite narrow, such that the detector 406 can easily cover the range. In fact, most of the contrast is embedded in the phase of the transmitted field. In order to properly perform a Fourier transform, this method utilizes the ability to measure not only the amplitude but also the quantitative phase image.

As described previously, tomographic phase microscopy with the system of FIG. 1 is used to obtain a three-dimensional distribution. As described above, a beam-splitter recombines the sample and reference laser beams, forming an interference image at the camera plane. A high speed CMOS camera (Photron 1024PCI) records 4 images separated by 200 μs, exactly one-quarter the reciprocal of the heterodyne frequency. The exposure time is 20 μs. In this way, four interference patterns $I_1$, $I_2$, $I_3$ and $I_4$ are recorded in which the sample-reference phase shift varies by $\pi/2$ between consecutive images. Then, by applying phase shifting interferometry, the phase $\phi_S(x,y)$ and amplitude $A_S(x,y)$ can be obtained from the relation $\phi_S(x,y)=\arg z_S(x,y)$ and $A_S(x,y)=abs(z_S(x,y))$, with $z_S(x,y)=(I_4-I_2)+i(I_3-I_1)$. The fast acquisition time between frames reduces the effect of external noise.

To obtain the angular light scattering spectrum, the angle of the galvanometer mirror 20 is selected such that the direction of the incident beam is parallel to the optical axis of the objective lens. As explained in the previous section, both amplitude $A_S(x,y)$ and phase $\theta_S(x,y)$ images of the sample are collected. Since there can be residual spatial variations in phase and amplitude of the reference beam and other scattering from the optical elements, a separate measurement with no sample in the field of view is used to obtain the amplitude $A_B(x,y)$ and phase image $\phi_B(x,y)$ of the background. The normalized amplitude $A(x,y)=A_S(x,y)/A_B(x,y)$ and background-subtracted phase $\phi(x,y)=\phi_S(x,y)-\phi_B(x,y)$ are then determined. To obtain the angular light scattering spectrum, a Fourier transform of the corrected field $E(x,y)=A(x,y)\exp(\phi(x,y))$ can be performed.

Figure 9:
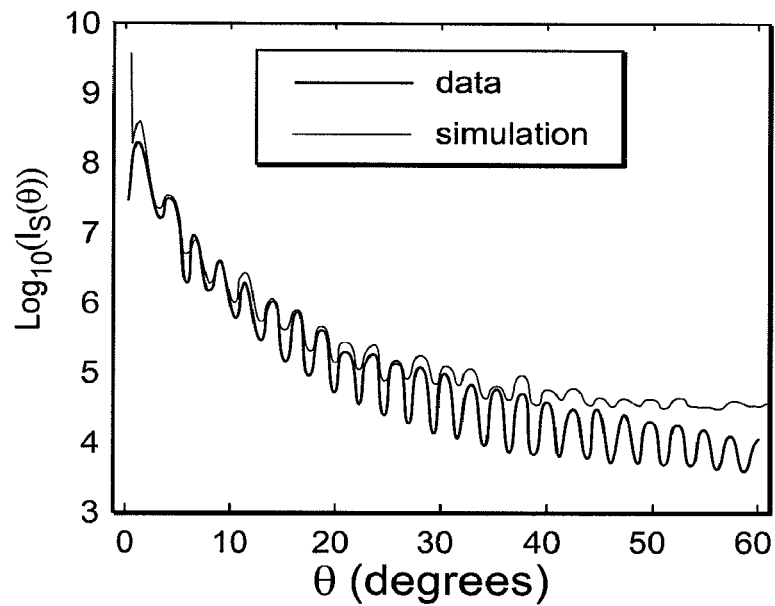
FIG. 9 is a comparison of measured angular light scattering spectrum of reference data to a Mie theory representation.

Reference data can be obtained by imaging a 10 μm sized polystyrene bead. Both amplitude $A(x,y)$ and phase $\phi(x,y)$ images of a bead are shown in FIGS. 8A and 8B. After converting them into the field, $E(x,y)=A(x,y)\exp(\phi(x,y))$, a Fourier transform was performed as shown in FIG. 8C. To get the angular spectrum, the spatial frequency was converted into scattering angle based on the relation $v_{x,y}=n \sin(\theta)/\lambda$, where n is refractive index of the medium, $\lambda$ is the wavelength in free space, and $\theta$ is a scattering angle. There are clear ring patterns associated with the round shape of the bead. The angular spectrum averaged over azimuthal angle $I_s(\theta)$ can be compared with that predicted by Mie theory in FIG. 9. There is agreement between theory and measurement indicating the accuracy of the method. There is a slight difference at large scattering angles (near 60 degrees), which may be due to the spatial noise of the E-field image. The size of signal at large angles is very small, and therefore it is more susceptible to measurement noise.

In a preferred embodiment, the angular spectrum of individual cells such as HeLa cells can be measured. The effect of acetic acid at low concentration was also measured. Acetic acid can be used to identify suspicious sites on the cervix by monitoring the whitening effect associated with precancerous lesions.

Both amplitude and phase images were measured at zero degree illumination and an averaged angular light scattering spectrum (FIG. 10D) was obtained. At the same time, refractive index tomograms of HeLa cells were also measured (FIGS. 4A-4C). Measurements were made before and after changing the cell environment from a normal culture medium (FIG. 4A) to a culture medium containing 0.38% acetic acid (FIG. 4B). The refractive index of the nucleolus increased from 1.36 to 1.39, and the heterogeneity of the rest of the nucleus and cytoplasm increased dramatically. After adding acetic acid, the angular scattering spectrum exhibits a significant increase in scattering at angles greater than 10 degrees. This increase can be explained qualitatively by the increase in heterogeneity of the 3D refractive index map. Another measurement can be made three minutes after replacing the acetic acid medium with the normal culture medium. The spatial variation reduced and the refractive index of the nucleolus reduced somewhat, but remained larger than its baseline value (FIG. 4C), and the angular light scattering spectrum returned to that of the original cells for the overall range of angles.

Considering that cells are weak absorbing objects under visible light illumination, it is apparent that the heterogeneity of the refractive index is the main source of light scattering. Therefore by solving the wave propagation equation with the measured 3D refractive index map as input, the angular light scattering spectrum can be obtained. Then, direct and quantitative comparison can be made with a separate scattering measurement.

The most accurate method for calculating the angular light scattering spectrum from the 3D refractive index map is the FDTD (finite domain time difference) method. However, the processing time is usually long. Instead, the Born approximation can be used to obtain the forward light scattering. When the incident beam is not significantly modified by the presence of the specimen, the Fourier transform of the object function, $O(x,y,z)=2\pi(n(x,y,z)^2-n_m^2)/\lambda$ with $n(x,y,z)$, the complex refractive index at the specimen, and $n_m$, the refractive index of the medium can be related to the Fourier transform of the transmitted field. See, for example, (A. C. Kak, M. Slaney, *Principles of Computerized Tomographic Imaging* (Academic Press, New York, 1999)) incorporated herein by reference.

Figure 11:
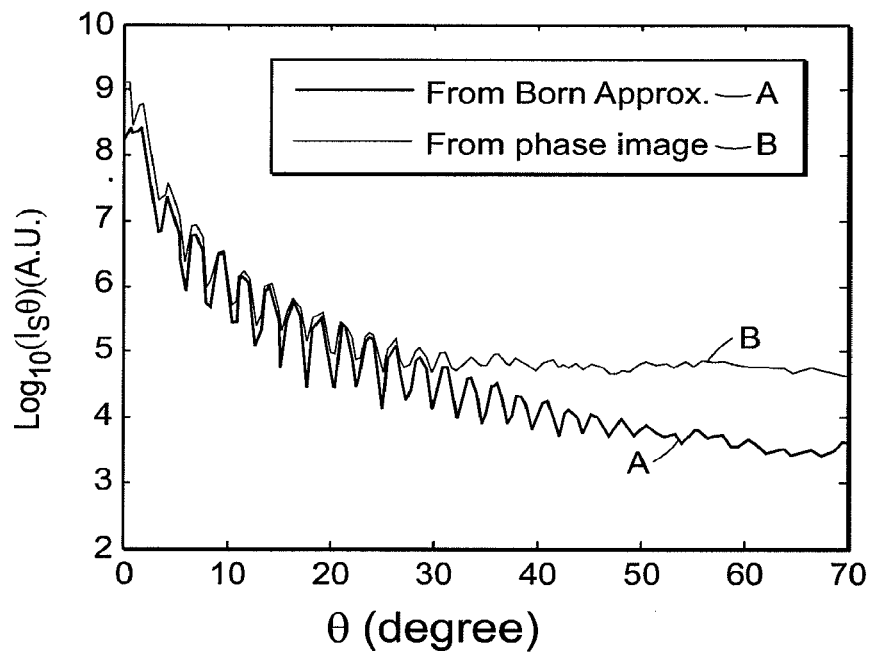
FIG. 11 is a graphical comparison of angular light scattering spectrum calculated from a tomogram based on a Born approximation and measured scattering of a bead.

The applicability of the Born approximation in obtaining angular light scattering spectrum can be established with a reference measurement by using a 10 μm polystyrene bead. A 3D map of the refractive index tomogram using tomographic phase microscopy can be measured, and processed to provide the forward scattering spectrum based on the Born approximation (FIG. 11). Compared to the spectrum calculated from the field-based image, there is agreement with respect to the oscillation period as a function of scattering angle. The discrepancies at large scattering angle may be due to the relatively large noise of the single E-field image as opposed to the tomogram and the slight reduction of spatial resolution in the tomographic reconstruction process.

Figure 10:
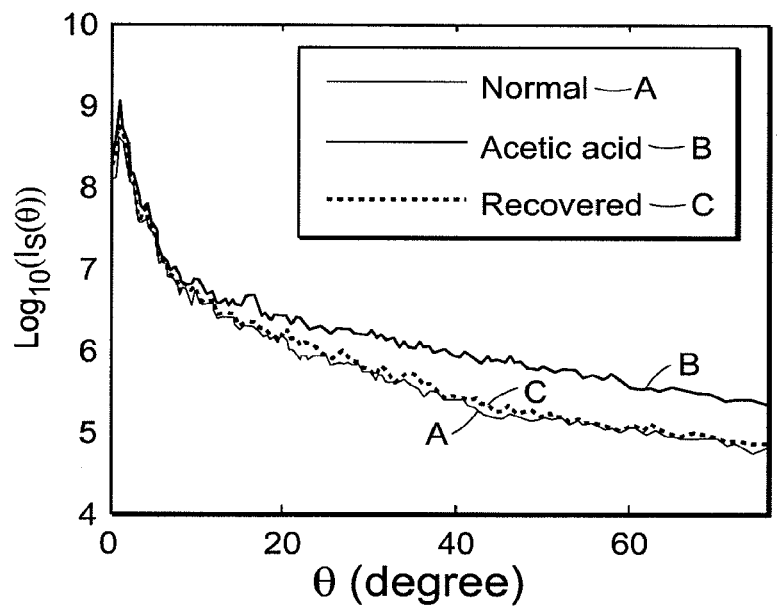
FIG. 10 is an angular light scattering spectrum of the images in FIGS. 4A-4C.
Figure 12:
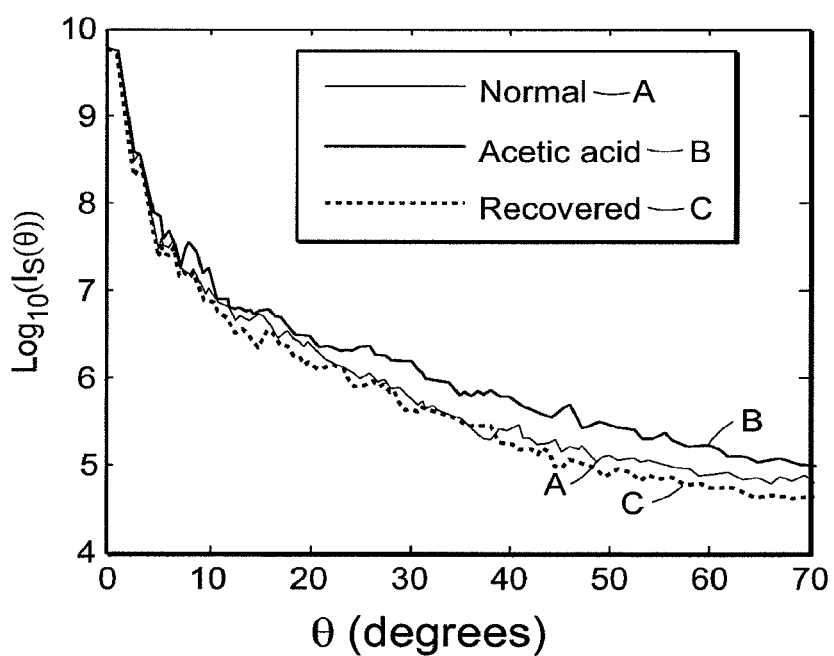
FIG. 12 graphically illustrates the angular light scattering spectrum determined from the tomograms of FIGS. 4A-4C based on Born approximation.

By determining the forward angular scattering spectrums (FIG. 12) of a HeLa cell at three different states from their refractive index tomograms shown in FIGS. 4A-4C. The tendencies are quite similar to the previous angular light scattering measurements (FIG. 10). The scattering increases as the acetic acid is added. The Fourier transform of the object function related to the refractive index determines the angular light scattering. If the structure is more heterogeneous, the high spatial frequency components of the object function will accordingly increase, which results in an increase in light scattering at large angle.

Thus, the present invention can use the relation between the structures of the cell to the angular light scattering spectrum. For example, from the refractive index tomogram, the refractive index of nucleus or nucleolus can be modified and the forward light scattering spectrum of the modified index map can be determined using the Born approximation. By comparing this with the original angular light scattering spectrum, this indicates that the refractive index map affects the light scattering spectrum. This method can be used to measure the size of organelles.

In a preferred embodiment of the invention, the tomographic phase microscope can be used for bright field and fluorescence imaging. For bright field imaging, a white light source 80 such as a light emitting diode (LED) or other broadband light source placed between the scanning mirror and a condenser lens serves as an illuminator, and images are recorded by a second detector such as a CCD camera (Photometric CoolSnap HQ) along a separate optical path. Bright field images provide a form of optical sectioning, due to the extremely short depth of field<1 μm) provided by NA 1.4 illumination and collection. For fluorescence imaging, a standard filter cube 84 (Olympus) with appropriate filters is placed under the objective lens, and fluorescence excitation is provided by a third light source 82, either a mercury arc lamp (Olympus) or a collimated blue LED (Lumileds). For single cells, widefield fluorescence imaging using DAPI or SYTO (Invitrogen) nucleic acid stains is used to identify nuclear boundaries. In certain applications, imaging of autofluorescence of a sample may be performed. Autofluorescence imaging methods are described, for example, in U.S. Pat. No. 7,235,045, which is hereby incorporated by reference.

Yet another preferred embodiment of the invention is a method for imaging a thick sample by using a propagation processing sequence. This is an alternative to the projection approximation described above. The propagation sequence can be more accurate for samples that are thick compared to the depth of focus of the imaging system and/or have a sufficiently large refractive index relative to that of the background.

The tomographic system described above is used to acquire data. The method includes numerically propagating the sample field to various axial distances, d, and form tomograms at multiple planes within the sample. This is the numerical equivalent of acquiring tomograms at multiple focal planes by physically translating the objective lens in the axial direction.

The focus at the (approximate) center of the sample, z=0, is first located and, as above, the E-field and quantitative phase images are obtained. A tomogram with well resolved features near the center of the sample can then be obtained. The propagation of this field is then calculated in free space by a distance d:

$$u_\theta(x, y; d) = \int\int U_\theta(k_x, k_y; z=0) e^{ik_x x + ik_y y + id\sqrt{k_m^2 - k_x^2 - k_y^2}} dk_x dk_y. \quad (1)$$

Here, $U_\theta(k_x, k_y; z=0)$ is the Fourier transform of the field, $u_\theta(x,y;z=0)$, and z=d is the axial location of the focus. Equation (1) provides a set of field amplitudes and quantitative phase images at the set of illumination angles, in which the focus has been moved or propagated to z=d. The filtered back-projection method is then applied to the quantitative phase image to obtain a tomogram with well resolved features near z=d. This procedure is repeated for successive values of d such that optimal focus is maintained throughout the depth of the sample.

The propagation method was used on a sample composed of 10 μm diameter polystyrene beads (n=1.588 at λ=633 nm)

in immersion oil (n=1.559 at λ=633 nm). FIG. 13A shows the quantitative phase image of a single bead for θ=0° when the focus is 4 μm above the center of the bead. A fringe pattern was observed around the bead, due to diffraction. The refractive index tomogram at this focus position also displayed prominent fringe pattern artifacts, as seen in the x-y slice of FIG. 13C.

After applying the propagation correction with d=4 μm, bringing the focus to the center of the bead, the fringe pattern in the quantitative phase image was greatly attenuated (FIG. 13B). Similarly, the x-y slice of the refractive index tomogram at the center of the bead is nearly uniform and free from fringe artifacts after applying the propagation correction (FIG. 13D). Measured values of the refractive index contrast between bead and oil were in agreement with manufacturer's specifications.

The propagation method was applied to imaging single cells of a human colon adenocarcinoma cell line, HT-29. The cells were dissociated from culture dishes and allowed to attach to the chamber surface (coverslips) for about 4 hours before imaging. Angle-dependent field images were then obtained with the objective focused approximately at the center of the cells. FIGS. 14A-D show four x-y slices of the resulting tomogram, uncorrected for propagation, at a succession of sample depths spaced by 2 μm. The slice shown in FIG. 14C is at the focal plane (z=0). A stack of bright field images of the same cell was recorded in less then 1 minute after acquiring the tomogram data. These are shown in FIGS. 14J-14M, and correspond to the tomographic slices FIGS. 14A-14D.

At the plane of focus (FIG. 14C), sharp structures such as two nucleoli, the boundary of the nucleus and a large vacuole can be seen, and there is a clear correspondence between the tomogram and the bright field image (FIG. 14L). As seen in FIG. 14B, however, out-of-focus slices exhibit a loss of transverse resolution in these structures, even for a defocus of only 2 μm.

FIGS. 14F-14H show the corresponding x-y slices of the tomogram in which the propagation correction has been applied so that the computed sampling depth matches the position of the slice. Overall sharpness was substantially improved, particularly at boundaries. The improved resolution of the laminar structure revealed in FIG. 14G by the propagation algorithm (compare FIG. 14B) can be identified in the bright field image, FIG. 14K. FIGS. 14E and 14I, x-z sections along the dashed lines indicated in FIGS. 14D and 14H, respectively, show clear distinctions of two nucleoli and details of the nuclear boundary at the top part of the cell after the correction.

The propagation method incorporates diffraction effects into the filtered back-projection algorithm that can be operated using a computer programmed to adjust the scanner through a sequence of positions that moves the focal plane through the medium, and therefore provides an alternative 3-D reconstruction method to diffraction tomography. This method can be applied to objects that cannot be satisfactorily imaged with conventional diffraction tomography. In conventional first-order diffraction tomography, either the phase delay induced by the sample must be smaller than 2.2 radians (first-order Born approximation) or the relative refractive index must be less than a few percent (first-order Rytov approximation). The propagation method presented herein is free from such restrictions. The increased resolution provided by this technique can be employed for imaging small organelles such as mitochondria and lysosomes, and in studying light scattering from cells and tissues.

The present invention thus provides for quantitative refractive index tomography of living cells and tissues. The 3-D structure mapped by tomographic phase microscopy can complement the images with the use of material added to selectively alter an optical property of the region of interest such as hematoxylin and eosin staining Refractive index data can be used to study light scattering properties of cells and tissues and characterize sample-induced aberrations in microscopy. Characterization and correction of such aberrations may be particularly important for modern superresolution techniques such as STED and structured illumination microscopy.

Another preferred embodiment is a method that provides tomographic microscopy by spatial fringe pattern demodulation. This method is capable of providing video rate tomograms. The time resolution of the tomographic phase microscopy system and methods described above is limited by the phase-shifting interferometry technique used to acquire quantitative phase images. For example, up to about 100 different illumination angles may be required for optimum image quality with the phase-shifting interferometry method, with each angle requiring the capture of four raw frames, for a total of about 400 frames per tomogram. Further, the phase-shifting interferometry technique requires a galvanometer settling time of, for example, about 100 ms after each change of illumination angle. In general, acquisition rates up to about 0.1 Hz can be obtained with such methods. In the video rate tomographic microscopy embodiment, however, the phase images are acquired using spatial fringe pattern demodulation. This reduces the number of raw images required (for example, about 100 frames per tomogram can be used) and the method can be performed without the need to include a galvanometer settling time between frames. In this method, the reference beam can be maintained at a fixed tilt normal to the direction of sample beam scanning so as to keep the spatial frequency of the fringe pattern in an optimal range. Images can be acquired at rates up to about 30 Hz with this method, enabling monitoring of changes in cell or tissue structure at video rates.

Figure 15:
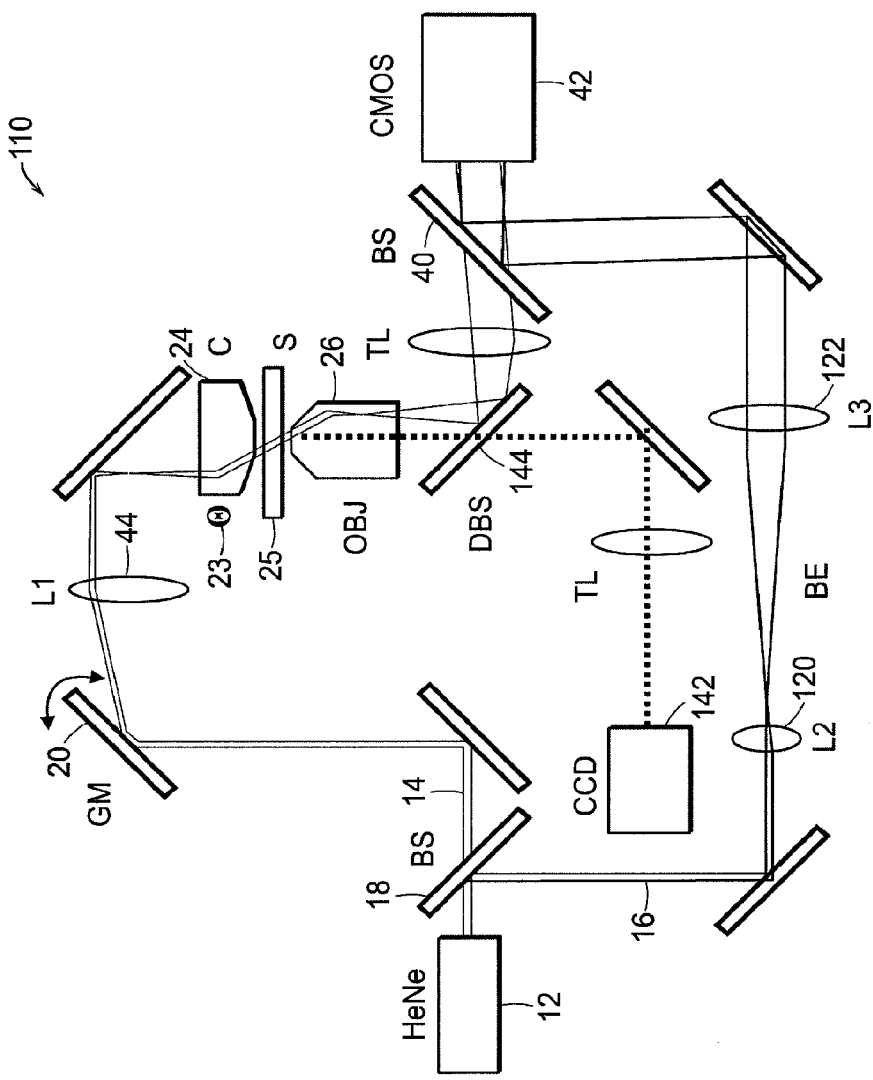
FIG. 15 illustrates a system for performing spatial modulation tomographic microscopy. The dotted line shows a pathway and components for optional bright field or fluorescence imaging.

A system 110 for spatial fringe demodulation tomographic phase microcopy is depicted in FIG. 15. The system, which is capable of video rate acquisition, is similar to the tomographic phase microscopy system shown in FIG. 1, but omitting the acousto-optical frequency shifting mechanism 28 in the reference beam path. A light source 12 such as a helium-neon laser beam (λ=633 nm) is divided into measurement 14 and reference arm 16 paths by a beamsplitter 18. An actuator 20 such as a galvanometer-mounted tilting mirror is used to vary the angle of illumination θ 23 of the medium 25 being measured, which is positioned between the oil-immersion condenser 24 and objective lenses 26. The reference laser beam is enlarged by a 10× Galilean beam expander containing lenses 120 and 122 and combined with the sample beam through a beamsplitter 40 to form a spatial fringe pattern at the image plane of camera 42. The galvanometer is driven by a symmetric triangle wave, for example at a frequency of 15 Hz and amplitude corresponding to +/−60 degrees at the sample. Both the rising and falling phases of the signal provide scans in angle (e.g., 30 scans/sec). For each angle of illumination a detector 42 such as a CMOS camera (e.g., Photron 1024PCI) and/or a CCD camera 142 situated downstream from a dichroic beamsplitter 144 records a plurality of images on memory of computer 100. Images can be acquired continuously at, e.g., 5000 frames/sec, providing 167 images during each galvanometer sweep. Irradiances at the detector plane can be about 10

μW/cm² for both the sample and reference fields. Exposure times of, for example, about 100 μsec can be used.

According to a spatial fringe pattern demodulation method, the Fourier transform of the raw image is first calculated. The Fourier transform contains peaks centered at 0 and $+/-q_\theta$, where $q_\theta$ is the angle-dependent fringe pattern spatial frequency, equal to the difference between the sample and reference wave vectors at the image plane. The next step in the method is to translate the $+q_\theta$ peak to 0 by shifting the Fourier components by $-q_\theta$. A 2D Hanning low pass filter can be applied to select only the central component. The third step is to apply the inverse Fourier transform to obtain a complex valued function $Z_\theta(x,y)$, and the final step is to calculate the phase image by $\phi_\theta(x,y) = \text{Arg } Z_\theta(x,y)$.

Figure 16A:
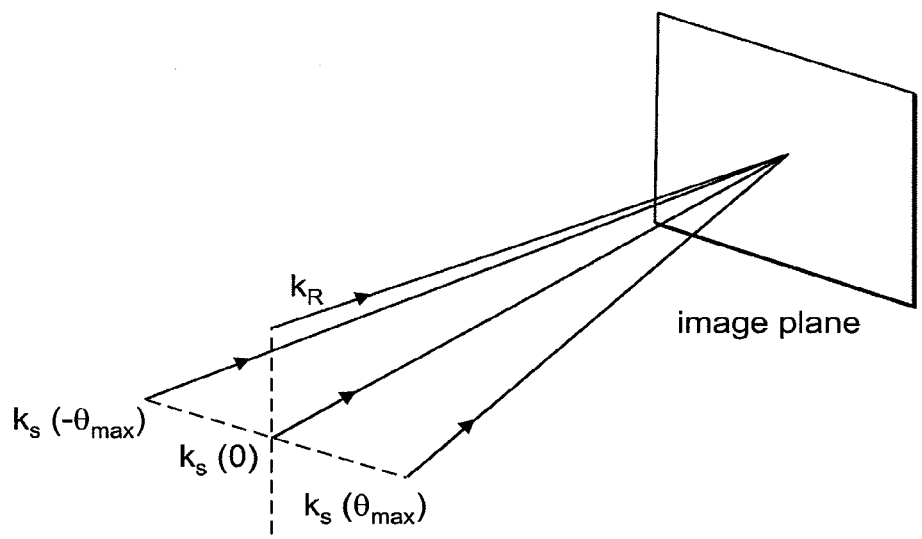
FIGS. 16A-G show beam geometry and images obtained for a 10 micron diameter polystyrene bead.
Figures 16B, 16C, 16D:
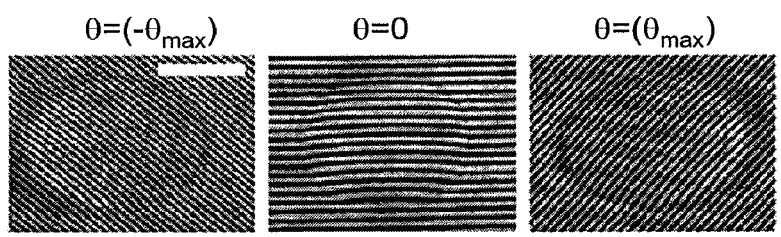
Figures 16E, 16F, 16G:
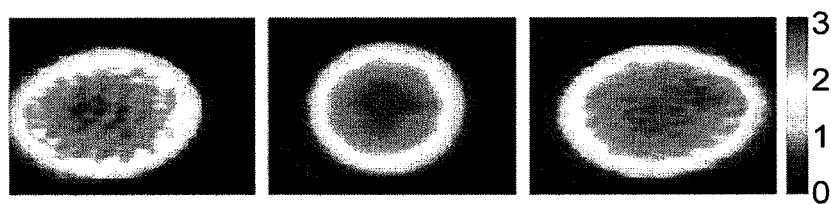

In the spatial fringe pattern demodulation method, the low-pass filter cutoff frequency limits the spatial resolution of the phase image. Therefore, it is preferable to use the maximum possible fringe frequency, subject to pixel spacing. For example, a fringe period of approximately 4 pixels can be used. Using the spatial demodulation method can result in low resolution for small θ. This can be avoided by using a fixed tilt of the reference beam in a direction normal to the sample beam tilt, with an angle matching the maximum tilt $\theta_{max}/M$ of the sample beam at the image plane, as shown in FIG. 16A. The resulting fringe pattern spatial frequency $$\vec{q}_\theta = \frac{k}{M}(\theta \hat{x} + \theta_{max} \hat{y})$$

has an amplitude always greater than or equal to $k|\theta_{max}|/M$ and rotates in direction by 90 degrees as the sample angle is varied from $-\theta_{max}$ to $+\theta_{max}$ (see FIGS. 16B-G). The low pass filter cutoff frequency can be held fixed at $k|\theta_{max}|/2M$ to ensure that the spatial resolution of the demodulated image remains independent of θ although the fringe pattern frequency varies by a factor of $\sqrt{2}$.

Optionally, a set of angle-dependent background phase images can be acquired with no sample present and subtracted from the sample phase images to reduce fixed-pattern noise, e.g., from dust, optical aberrations, and imperfect alignment.

The phase images (optionally background-subtracted) can be used to reconstruct the 3D refractive index of the sample using a filtered backprojection method after transformation of phase projection data to a plane normal to the illumination direction by dividing the coordinate in the tilt direction by cos θ. The result is the sample refractive index relative to the surrounding medium.

Figure 17E:
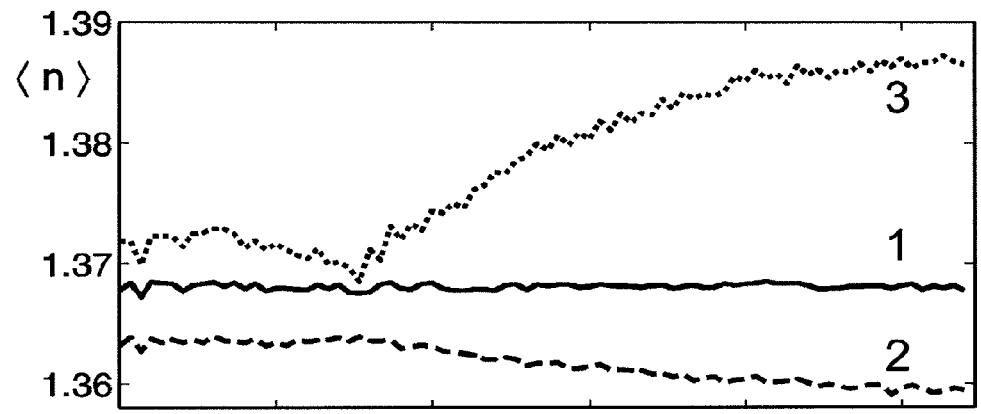
Figure 17F:
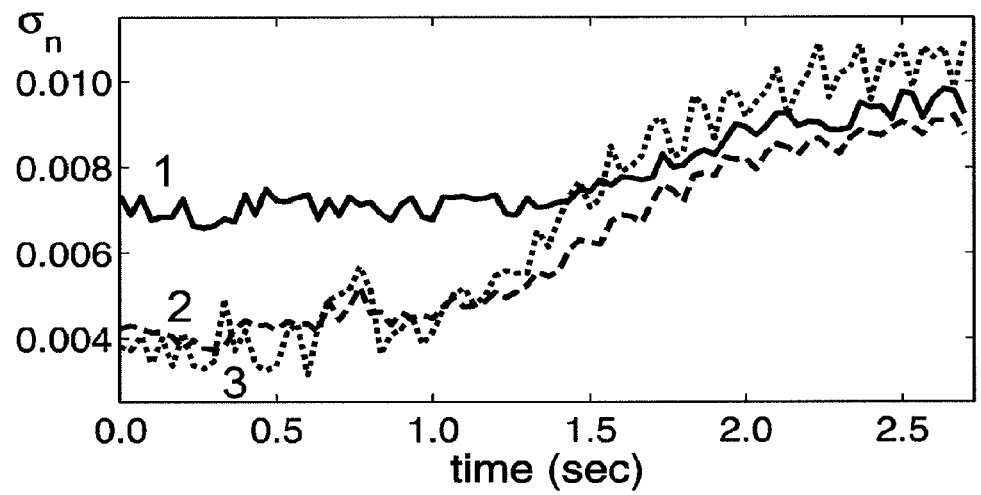

FIGS. 17 A-F show the time dependence of structural changes in a HeLa cell exposed to acetic acid solution at room temperature obtained using fringe pattern demodulation. Tomograms were obtained at 30 Hz while changing the medium from DMEM+10% fetal calf serum to the same medium containing 0.5% acetic acid at room temperature. Almost all changes in cell structure were found to occur during a 2.75 sec interval containing 82 frames. FIGS. 17A-C show optical slices through the center of the cell at the start, midpoint, and end of the 2.75 sec interval. An increase in refractive index heterogeneity throughout the cell was observed, and the index of the nucleolus increased dramatically. FIG. 17D outlines certain areas of interest in the HeLa cell of FIGS. 17A-C (1, region between cell membrane and nuclear membrane; 2, region enclosed by the nuclear membrane but not including the nucleolus; 3, the nucleolus). Boundaries between regions of interest were drawn manually based on correlation between index tomograms and bright field or fluorescence images using the nucleic acid stain SYTO (Invitrogen). FIG. 17E shows the time dependence of average refractive index for each of the areas of interest shown in FIG. 17D. FIG. 17F shows the standard deviation of refractive index in the areas of interest as a function of time.

Another preferred embodiment utilizes the spatial fringe pattern demodulation method described above to provide high resolution images of a sample, such as a cell, tissue, or organism, with molecular specificity. The method employs a UV laser, such as a laser with 325 nm emission (e.g., a He—Cd laser), and tomography is performed on the sample at two, three, or more different wavelengths of irradiation (e.g., 325 nm, 445 nm, and 663 nm). Each type of molecule possesses a unique change of refractive index over a range of wavelengths, which is generally known as dispersion. Thus use of two or more different wavelengths enables quantification of the concentration of different types of molecules and their distribution within a sample, such as a cell. For example, nucleic acids such as DNA present in the nucleus of a cell can be selectively visualized and its morphology, distribution, state of condensation, and overall amount per cell can be investigated. Using separate wavelengths, protein distribution, amount, and association with other structures also can be investigated. This technique can be used to diagnose cancer, developmental abnormalities, diseases, or medical conditions in which the expression, amount, or cellular distribution of, e.g., DNA is informative. A system such as the ones depicted in FIG. 1 or FIG. 15 can be used for such determinations. Optionally, for applications including the use of one or more fluorescent labels, beamsplitter 144 can function as a dichroic mirror that permits emitted fluorescence to be specifically imaged at camera 142. Different dichroic mirrors or filters can be applied to light transmitted through objective 26, providing a plurality of images that can be analyzed separately or aligned and superimposed to form a composite image for analysis.

The high resolution method just described, utilizing UV irradiation and spatial fringe pattern demodulation, can be adapted to localize specific molecular targets in a sample, such as a cell or tissue. For example, an antibody directed to such a molecular target, e.g., a specific protein, carbohydrate, nucleic acid or other antigen, can be conjugated to a label. The optical properties of the label can then be employed to visualize the target and its amount or distribution within the sample. For example, the label can be a fluorescent label, having an excitation wavelength such that the laser irradiation used for tomography excites the fluorophore. A dichroic mirror or filter can be positioned in the sample beam pathway after the objective lens, permitting an image of the fluorophore distribution and amount to be superimposed on a phase image of the cell. Alternatively, the label can be a nanoparticle whose refractive index is sufficiently distinct (e.g., higher) than that of other cellular structures that the nanoparticles can be visualized in the phase image of the cell.

Still another preferred embodiment is a method of acquiring full-field amplitude and quantitative phase images of samples in translational motion, in contrast to the methods described above, which require the sample to be essentially stationary during image acquisition. The method includes the use of a focused beam to generate transmitted electric field images of one or more sample structures, such as cells, at successive points of translation across the stage of a microscope. The method produces plane wave images with any incident direction within the numerical aperture of the objective lens. After applying filtered back-projection to the set of synthesized angular plane wave images, 3D maps of refractive index of live cells are obtained. This method, referred to as synthetic aperture tomography, can be combined with flow cytometry or microfluidic devices, and enables high throughput acquisition of quantitative phase data from large numbers of cells.

According to Huygens' principle, a directional plane wave can be synthesized from a set of position-dependent focused beams. If one or more samples are translated across the focused beam and the phase and amplitude are recorded at each position, then plane waves with any incident direction can be synthesized. From a set of angular phase images of synthesized plane waves, a 3D image can be constructed using filtered back projection.

Any wavefront can be synthesized by a set of spherical waves. A tightly focused Gaussian beam can be approximated as a spherical wave. A set of focus fields can be used to generate a plane wave propagating in any direction. Consider a 2-D object with the x-axis as a transverse plane and z as an axial plane. Then, a focused beam can be represented as a weighted set of plane waves as follows:

$$E(x,z) = \int A(k_x) e^{-(ik_x x + ik_z z)} dk_x, \quad (2)$$

with $A(k_x)$ the amplitude of an individual plane wave whose spatial frequency is $k_x$. The wave number in the medium, $k_0 = 2\pi/\lambda'$ is fixed with $\lambda' = \lambda_0/n_{medium}$, the wavelength in the medium; $k_z$ is determined by the relation $k_z = [k_0^2 - k_x^2]^{1/2}$. After interacting with a specimen, the transmitted field at the detector, location $z=z'$, can be written as a weighted sum of plane waves:

$$E(x,z') = \int A(k_x) e^{-(ik_x x + ik_z z' + i\phi(x;k_x))} dk_x, \quad (3)$$

with $\phi(x;k_x)$ a complex phase induced by the sample for each plane wave component $k_x$.

Since many of the plane waves are added together, not all of the plane wave components can be retrieved. If the source is moved along the x-direction by $\eta$, the plane wave decomposition changes as follows:

$$E(x;\eta,z') = E(x-\eta,z') = \int (A(k_x) e^{ik_x \eta}) e^{-(ik_x x + ik_z z' + i\phi(x;k_x))} dk_x. \quad (4)$$

The additional phase term $e^{ik_x \eta}$ is introduced as the source moves. This means that the larger the spatial frequency $k_x$ is, the more phase shift is introduced. Fourier transform of $E(x;\eta,z')$ for $\eta$ separates the individual spatial frequency components out of integration as follows.

$$\int E(x;\eta,z') e^{-ik_\eta \eta} d\eta = \quad (5)$$
$$\int \left( \int e^{-i(k_\eta - k_x)\eta} d\eta \right) A(k_x) e^{-(ik_x x + ik_z z' + i\phi(x;k_x))} dk_x =$$
$$A(k_\eta) e^{ik_\eta x + i\sqrt{k_0^2 - k_\eta^2} z' + i\phi(x;k_\eta)}$$

Here, the relation $\int e^{-i(k_\eta - k_x)\eta} d\eta = \delta(k_\eta - k_x)$ is used. As a result, the integration over $k_x$ disappears and a complex phase $\phi(x;k_\eta)$ of each spatial frequency component $k_\eta$ is obtained. Although Fourier transform is used, the process of getting each plane wave can be interpreted as a synthesis of focused beams with a translation-dependent additional phase factor, $e^{-ik_\eta \eta}$. Thus, this method is referred to as synthetic aperture tomography.

Using the relationship $k_\eta = k_0 \sin\theta$ with $\theta$ representing the propagation direction of the plane wave relative to the optic axis, the angular phase image $\phi(x;\theta)$ can be determined. If the phase image is interpreted as an integration of the refractive index along the beam propagation direction, then a filtered back-projection process (see above) can be used to obtain the 3-D map of refractive index.

In theory, a focused beam can be obtained by focusing the collimating beam with a spherical lens, and scanning can be performed in a 2-D transverse plane. In the method according to the invention, however, the illuminating beam can be focused with a cylindrical lens instead, such that one axis is a focused beam and the other axis a plane wave. The axis along the focused beam direction is referred to as a focal axis and the other as a planar axis. In doing so, two advantages are obtained. First, scanning is only required along the focal axis, and therefore the requirement for scanning is reduced from 2-D to 1-D; and second, the reconstruction problem is reduced from 3-D to 2-D since the planar axis can be treated independently. The focal axis corresponds to the x-axis in the theory described above.

Figure 18A:
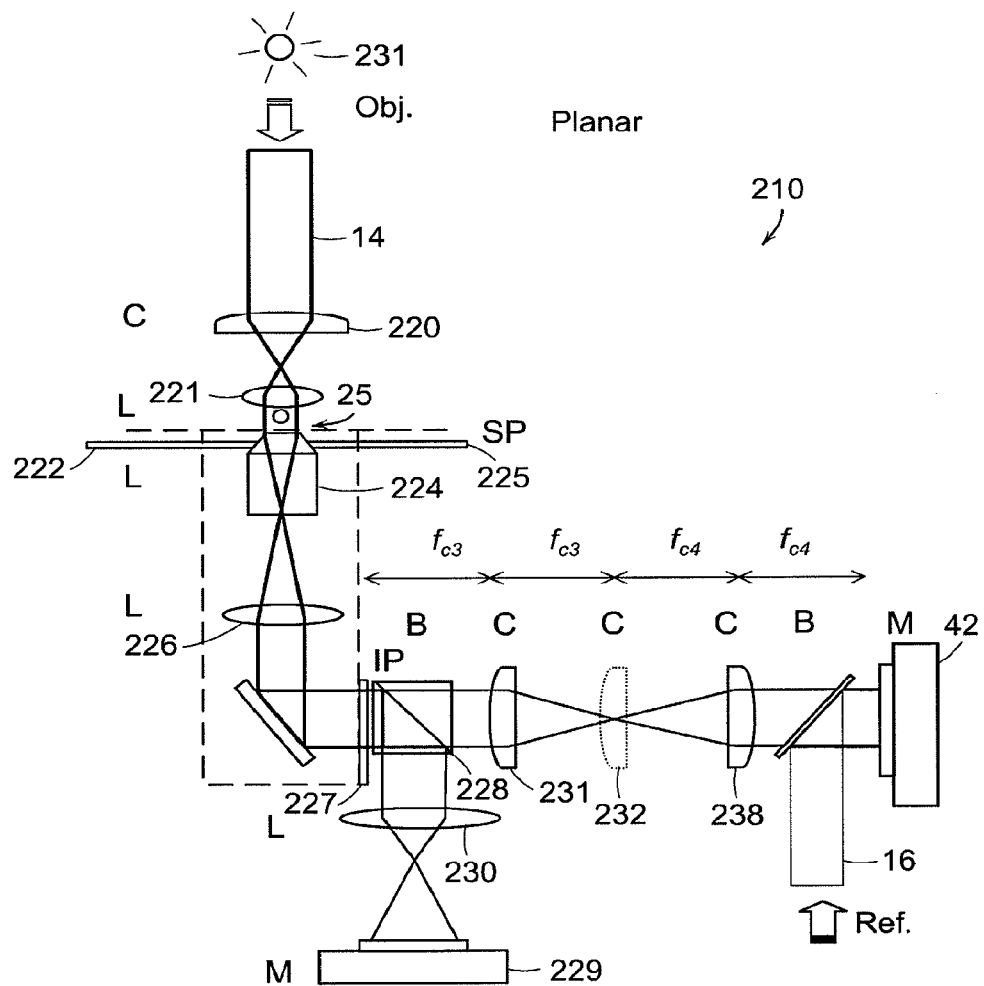
FIGS. 18A-G illustrate a system for synthetic aperture tomography.
Figure 18B:
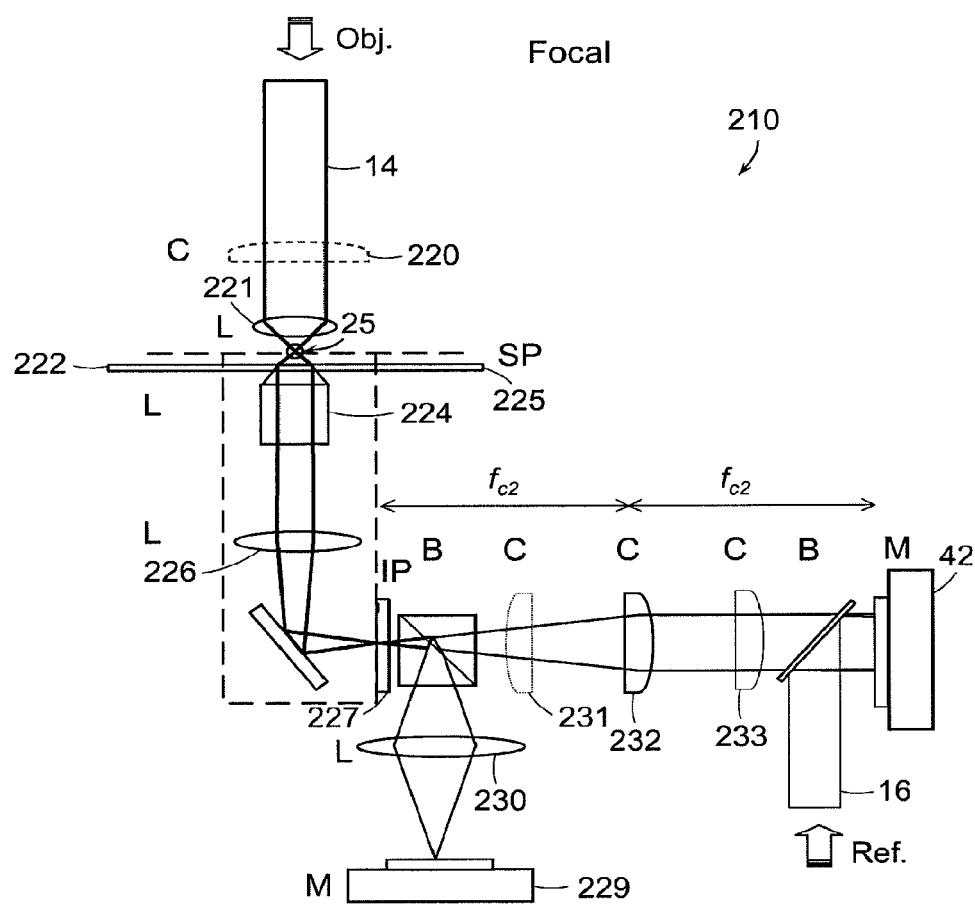
Figure 18C:
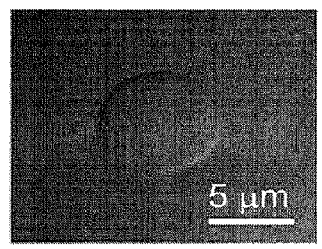
Figure 18D:
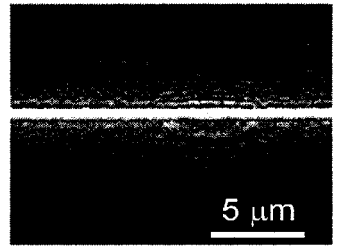

A system 210 for synthetic aperture tomography is depicted schematically in FIGS. 18A-B. The system is based on a heterodyne Mach-Zehnder interferometer, and is similar to the system shown in FIG. 1, but with the omission of galvanometer-driven mirror 20. The light source (e.g., a HeNe laser (Milles Griot, USA)), the beamsplitter that splits the source into reference and sample beams, and the pair of acousto-optic modulators that frequency shift the reference beam are as in the system shown in FIG. 1 and are not shown in FIGS. 18A-B. Sample beam 14 travels through sample 25 located on the sample stage of an inverted microscope (e.g., Zeiss Axiovert S100, Germany). The sample beam is shaped as a line focus beam at the sample plane 225 using a cylindrical lens 220 and a high NA condenser lens 221 (e.g., 1.4 NA oil immersion, Nikon Japan) such that one axis (focal axis, see FIG. 18B) is a focused beam and the other axis (planar axis, see FIG. 18A) a plane wave. This is to reduce the number of axes to be scanned. To simulate the flow of live cells for future application, samples were translated across the line focus beam by an optional precision micro-position translation stage 222 (e.g., PI M-216, Physik Instrumente, Germany) with a step of 0.1 μm. The direction of translation was orthogonal to the planar axis. In an alternative embodiment, the system can contain a flow cell or microfluidics system 223 containing an optical window either with or without a precision translation stage (see FIG. 18G). For example, cells in a medium can be pumped through the flow cell as in flow cytometry, while they are monitored or analyzed individually using synthetic aperture tomography as they transit through the optical window. After the sample beam is transmitted through the sample, the beam is magnified by an objective 224 (e.g., Zeiss 100× oil immersion) and tube lens 226, and relayed to image plane 227 at the video output port of the microscope. Optionally, beam splitter cube 228 can be placed right after the video port, and reflected light can be directed to camera 229 and used to monitor the image plane. The image is relayed to video camera 229 (e.g., TC-87, Sony) via lens 230 located right after the beam splitter. FIG. 18C is a typical bright field image of a 10 μm bead measured at 229. To record the bright field image, an illumination source such as LED 231 (not shown in the figure) is used instead of the laser, and cylindrical lens 220 is taken out temporarily. FIG. 18D shows a line focused beam illuminating about the center of the beam when the cylindrical lens is in position.

The beam transmitted through the beam splitter 228 is used to measure the phase and amplitude of the field at the image plane. Note that a line focus beam at the image plane has a highly non-uniform intensity distribution. Due to limited dynamic range of the camera (e.g., 12 bit), it cannot properly digitize the intensity distribution of the light. To properly measure the phase image, a relatively uniform distribution of beam intensity preferably is obtained across the detector. The focused beam can be expanded in focal axis by positioning a cylindrical lens 232, which provides an optical Fourier transform of the image. The beam then becomes wide and flat in its intensity distribution at the camera plane. For the planar axis (FIG. 18A), the image is relayed with two cylindrical lenses 231 and 233 since the beam is already uniform in its intensity distribution. As a result, the focal axis is in spatial frequency coordinate ($k_x$) while the planar axis is in spatial coordinate (y).

Figure 18E:
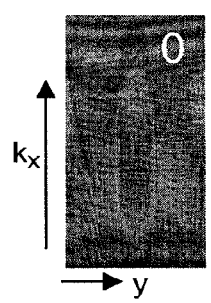
Figure 18F:
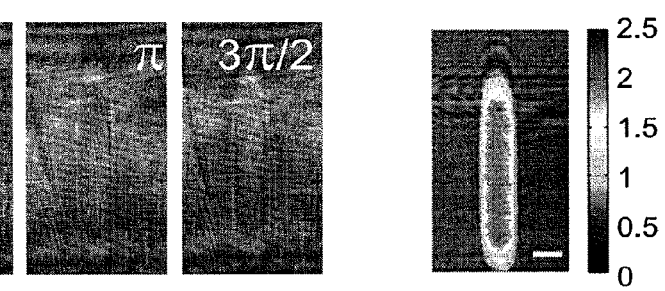
Figure 18G:
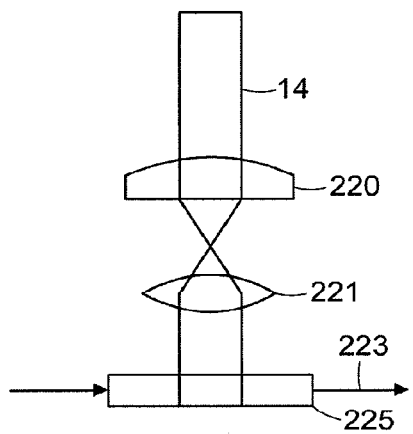

After combining a planar reference beam 16 whose frequency is shifted by 1.25 kHz using two acousto-optic modulators as described above, a fast CMOS camera 42 (e.g., Photron 1024PCI) can record 4 interferometric images with 5 kHz frame rates. A typical set of 4 interferogram images is shown in FIG. 18E, for a line focus beam positioned at about the center of a 10 µm bead. After applying a four frame phase shifting interferometry (PSI) analysis, the phase image $\phi(k_x, y)$ as shown in FIG. 18F was obtained.

A live HeLa cell was imaged with synthetic aperture tomography during translation. Cells were dissociated from culture dishes and incubated for 4 to 5 hours in imaging chambers so that individual cells had become attached to their glass substrates prior to imaging. A set of phase images $\phi(k_x, y; \eta)$ was taken as a function of sample translation $\eta$ and is shown in FIG. 19A. The range of translation was more than twice the diameter of the sample, and the translation occurred in 0.1 µm steps. Corresponding amplitude images $A(k_x,y;\eta)$ were also obtained from the PSI analysis. After combining both amplitude and phase to obtain an electric field $E(k_x,y;\eta)=Ae^{i\phi}$ a numerical inverse Fourier transform was carried out along the $k_x$-axis to obtain $E(x;\eta,y)$. FIG. 19B shows a resulting amplitude image as a function of the sample translation, $\eta$. The focused beams were shifted along the x direction with increasing q based on prior knowledge of the µ. During the measurement, the illumination beam was stationary and the sample was moving. In order to employ the theory of synthetic aperture tomography, however, the sample should be stationary while the illumination beam is translated. Since the amount of the sample translation q was known from the translation stage, the image was numerically shifted in the opposite direction compared to the direction of translation. This is equivalent to shifting the focused beam along the x-direction while the sample is stationary.

With a set of E-field images $E(x;\eta,y)$ taken for the sample in translational motion, synthetic aperture analysis was performed as described above. For an any given y, the Fourier transform of $E(x;\eta,y)$ was taken for the sample translation $\eta$ as described in Eq. (5).

$$\tilde{E}(x; k_\eta, y, z') = \int E(x; \eta, y, z')e^{-ik_\eta\eta}d\eta = A(k_\eta)e^{-ik_\eta x - i\sqrt{k_0^2 - k_\eta^2}\, z' - i\phi(x,y;k_\eta)}$$

By dividing by the same processed images taken without the sample, the phase image $\phi(x,y;k_\eta)$ induced by the sample can be obtained (FIG. 19C). Using the relationship $k_\eta = k_0 \sin\theta$, with $\theta$ the direction of the plane wave relative to the optic axis, the angular projection phase image, $\phi(x, y; \theta)$, can be determined.

FIGS. 19C and 19D show the phase image $\phi(x, y; \theta)$ for a HeLa cell at angles $\theta$ of zero and 35 degrees, respectively. Note that the phase image for nonzero values of $\theta$ is elongated along the direction of tilt (x-axis). This is due to the fixed image plane during tilting illumination. A set of angular projection phase images ranging from −40 to 40 degrees can be synthesized from this system. After applying filtered back-projection, a 3D map of refractive index can be obtained.

FIGS. 20A-G show the x-y slices of a reconstructed tomogram of a HeLa cell with an axial distance of one micron between each slice image. Detailed structures such as the nucleus and nucleolus are clearly visible, especially in FIG. 20D. A bright field image at approximately the same focus is presented in FIG. 20H to show the close correspondence with the tomogram. By using the refractive index of the culture medium (1.337) measured in a separate study, the refractive index of the HeLa cell was found to be in the range of 1.36-1.38. Similar to the results shown above using tomographic phase microscopy, the heterogenous structures in the cytoplasm were found to have a higher refractive index than the nucleus.

Due to the Gaussian intensity profile of the illumination used for synthetic plane waves, the sensitivity of signal detection is reduced at large angles. As a result, the axial resolution of synthetic aperture tomography is about 1 µm.

While the invention has been described in connection with specific methods and apparatus, those skilled in the art will recognize other equivalents to the specific embodiments herein. It is to be understood that the description is by way of example and not as a limitation to the scope of the invention and these equivalents are intended to be encompassed by the claims set forth below.

The invention claimed is:

1. A synthetic aperture method for measuring refractive index of a medium comprising:
   transmitting a focused beam of light along a first light path through a medium;
   combining the light transmitted through the medium with a reference light;
   detecting the combined light;
   determining a phase image and an amplitude image of the medium;
   combining the phase and amplitude images to form an electrical field image of the medium; and
   determining the distribution of a refractive index of the medium using synthetic aperture analysis.

2. The method of claim 1 wherein the medium is in translational motion and a series of refractive index distributions of the medium are formed.

3. The method of claim 1, further comprising positioning a sample in the medium to be measured relative to the first scanning light path.

4. The method of claim 3, wherein the sample is in translational motion and a series of refractive index distributions of the sample are formed.

5. The method of claim 3, wherein the sample is a biological sample.

6. The method of claim 3, wherein an index of refraction of the sample is altered by less than 5%.

7. The method of claim 6, wherein an index of refraction of the sample is altered by less than 1%.

8. The method of claim 7, wherein an index of refraction of the sample is not altered.

9. The method of claim 5, further comprising adding a substance to the medium or to the biological sample prior to said step of determining, wherein adding the substance alters an index of refraction of the biological sample by less than 5%.

10. The method of claim 9, wherein adding the substance alters an index of refraction of the biological sample by less than 1%.

11. The method of claim 5, further comprising adding a substance to the medium or to the biological sample prior to said step of determining, wherein adding the substance alters an index of refraction of the biological sample.

12. The method of claim 5, wherein the biological sample is a cell, a plurality of cells, a tissue, or an organism.

13. The method of claim 5, wherein the biological sample comprises two or more distinct cell types.

14. The method of claim 5, wherein the medium is a culture medium.

15. The method of claim 3, further comprising flowing the medium and the sample across the first light path.

16. The method of claim 5, wherein an index of refraction in a single cell is measured.

17. The method of claim 5, wherein an autofluorescence in a single cell is measured.

18. The method of claim 5, wherein a scattering spectrum in a single cell is measured.

19. The method of claim 5, wherein a size or volume is measured for the biological sample or a portion thereof.

20. The method of claim 5, wherein a cell size distribution is measured for the biological sample or a portion thereof.

21. The method of claim 5, wherein a characteristic of a nucleic acid is measured in the biological sample or a portion thereof.

22. The method of claim 1, further comprising obtaining a plurality of images of the sample at a rate of at least four frames per second.

23. The method of claim 1, further comprising determining a distribution of fluorescence in the medium.

24. The method of claim 23, wherein the medium comprises a biological sample, and the fluorescence is autofluorescence of the sample or is caused by a fluorescent label added to the sample.

25. The method of claim 1, further comprising modulating a frequency of the reference light.

26. A method of diagnosing a disease or medical condition comprising performing the method of claim 1, wherein the medium comprises a cell or tissue sample from a subject suspected of having said disease or medical condition.

27. The method of claim 26, wherein the subject is suspected of having cancer.

28. The method of claim 27, wherein the subject is suspected of having cervical or uterine cancer.

29. The method of claim 28, wherein the cell or tissue sample is positioned in the medium to be measured relative to the first scanning light path, and a change in a refractive index distribution in the sample is determined after introduction of acetic acid into the medium.

30. A method of performing flow cytometry, comprising carrying out the method of claim 1, wherein a series of refractive index distributions are determined for a plurality of cells in translational motion.

* * * * *

UNITED STATES PATENT AND TRADEMARK OFFICE
CERTIFICATE OF CORRECTION

PATENT NO.         : 9,546,952 B2
APPLICATION NO.    : 14/490242
DATED              : January 17, 2017
INVENTOR(S)        : Choi et al.

It is certified that error appears in the above-identified patent and that said Letters Patent is hereby corrected as shown below:

In the Specification

In Column 1, Lines 17-20, delete:
"The invention was made with support from National Science Foundation Grant DBI-0754339 and National Institutes of Health Grant P41-RR02594-18. The United States Government has certain rights in the invention."

And insert:
-- This invention was made with government support under RR002594 awarded by the National Institutes of Health, and DBI0754339 awarded by the National Science Foundation. The government has certain rights in the invention. --

Signed and Sealed this
Fourth Day of November, 2025

John A. Squires
*Director of the United States Patent and Trademark Office*